United States Patent
Miyawaki et al.

(10) Patent No.: US 11,203,621 B2
(45) Date of Patent: Dec. 21, 2021

(54) PH-RESPONSIVE PROTEOLYSIS PROBE

(71) Applicant: RIKEN, Saitama (JP)

(72) Inventors: Atsushi Miyawaki, Saitama (JP); Hiroyuki Katayama, Saitama (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 15/737,082

(22) PCT Filed: Jun. 17, 2016

(86) PCT No.: PCT/JP2016/068189
§ 371 (c)(1),
(2) Date: Dec. 15, 2017

(87) PCT Pub. No.: WO2016/204296
PCT Pub. Date: Dec. 22, 2016

(65) Prior Publication Data
US 2018/0251500 A1 Sep. 6, 2018

(30) Foreign Application Priority Data
Jun. 19, 2015 (JP) .............................. JP2015-124261

(51) Int. Cl.
*G01N 33/533* (2006.01)
*G01N 33/542* (2006.01)
*G01N 33/84* (2006.01)
*G01N 21/64* (2006.01)
*C07K 14/435* (2006.01)
*C07K 19/00* (2006.01)
(Continued)

(52) U.S. Cl.
CPC ........ *C07K 14/43504* (2013.01); *C07K 14/00* (2013.01); *C07K 19/00* (2013.01);
(Continued)

(58) Field of Classification Search
CPC ....................................................... C12Q 1/37
(Continued)

(56) References Cited

U.S. PATENT DOCUMENTS

| 2005/0106661 A1 | 5/2005 | Miyawaki et al. |
| 2012/0178119 A1 | 7/2012 | Miyawaki et al. |
| 2014/0335539 A1 | 11/2014 | Watanabe et al. |

FOREIGN PATENT DOCUMENTS

| EP | 2527434 | 11/2012 |
| EP | 2790018 | 5/2017 |

(Continued)

OTHER PUBLICATIONS

Nguyen et al, Development of Fluorescent Substrates and Assays for the Key Autophagy-Related Cysteine Protease Enzyme, ATG4B. Assay and Drug Development Technologies 2014 vol. 12 No. 3 p. 176-189.*

Hancock et al., "A quantitative TR-FRET plate reader immunoassay for measuring autophagy" Autophagy, vol. 8, No. 8, Aug. 31, 2012, pp. 1227-1244.

Dolman et al., "Tools and techniques to measure mitophagy using fluorescence microscopy" Autophagy, vol. 9, No. 11, Nov. 3, 2013 pp. 1653-1662.

(Continued)

*Primary Examiner* — Sheridan Swope
(74) *Attorney, Agent, or Firm* — Casimir Jones, S.C.; Robert A. Goetz

(57) ABSTRACT

The present invention provides a tool which exhibits excellent properties in the quantification of autophagy activity. A unimolecular FRET probe of the present invention includes an acceptor consisting of a fluorescent protein to be enzymatically degraded inside a lysosome or a vacuole; and a donor having an amino acid sequence having a sequence (Continued)

identity of 95% or more with respect to an amino acid sequence represented by SEQ ID NO: 1.

6 Claims, 12 Drawing Sheets

Specification includes a Sequence Listing.

(51) Int. Cl.
*C12Q 1/06* (2006.01)
*C07K 14/00* (2006.01)
*C12Q 1/00* (2006.01)
*C12N 15/09* (2006.01)
*C12N 15/88* (2006.01)
*C12Q 1/02* (2006.01)
*C12Q 1/37* (2006.01)

(52) U.S. Cl.
CPC ............ *C12N 15/09* (2013.01); *C12N 15/88* (2013.01); *C12Q 1/00* (2013.01); *C12Q 1/025* (2013.01); *C12Q 1/06* (2013.01); *C12Q 1/37* (2013.01); *G01N 33/533* (2013.01); *G01N 33/542* (2013.01); *G01N 33/84* (2013.01); *G01N 21/6408* (2013.01); *G01N 21/6428* (2013.01)

(58) Field of Classification Search
USPC .......................................................... 435/23
See application file for complete search history.

(56) References Cited

FOREIGN PATENT DOCUMENTS

| WO | 2003/33693 | 4/2003 |
|----|------------|--------|
| WO | 2011/19082 | 2/2011 |
| WO | 2013/84950 | 6/2013 |
| WO | 2013/087921 | 6/2013 |

OTHER PUBLICATIONS

Extended European Search Report, EP Patent Application No. 16811770.3 dated Oct. 18, 2018.

Nguyen, T. G. et al., Development of fluorescent substrates and assays for the key . . . , ATG4B, Assay and drug development technologies, 2014, vol. 12, No. 3, p. 176-189, ISSN: 1540-658X.

Katayama, H. et al., A sensitive and Quantitative Technique . . . , Chemistry & Biology, 2011, vol. 18, p. 1042-1052, ISSN: 1074-5521.

Li, M. et al., A high-throughput FRET-based assay for determination . . . , Autophagy, 2012, vol. 8, No. 3, p. 401-412, ISSN: 1554-8627.

International Search Report for PCT/JP2016/068189, dated Sep. 13, 2016.

English Translation of International Preliminary Report on Patentability for PCT/JP2016/068189, dated Dec. 28, 2017.

* cited by examiner

FIG. 9

| 2xCoxVIII signal seq | mKeima | | |
|---|---|---|---|
| 2xCoxVIII signal seq | Ypet | linker | AFFP |
| 2xCoxVIII signal seq | Ypet | linker | AFFP | CL1 |
| 2xCoxVIII signal seq | Ypet | linker | AFFP | PEST |
| 2xCoxVIII signal seq | Ypet | linker | AFFP | CL1 | CL1 |
| 2xCoxVIII signal seq | Ypet | linker | AFFP | CL1 | PEST |

SEQUENCE LISTING

```
<160> NUMBER OF SEQ ID NOS: 9

<210> SEQ ID NO 1
<211> LENGTH: 226
<212> TYPE: PRT
<213> ORGANISM: artificial sequence
<220> FEATURE:
<223> OTHER INFORMATION: Artificially Synthesized Sequence
```

<400> SEQUENCE: 1

```
Met Val Ser Val Ile Lys Pro Glu Met Lys Ile Lys Leu Cys Met Arg
1               5                   10                  15

Gly Thr Val Asn Gly His Asn Phe Val Ile Glu Gly Glu Gly Lys Gly
                20                  25                  30

Asn Pro Tyr Glu Gly Thr Gln Ile Leu Asp Leu Asn Val Thr Glu Gly
            35                  40                  45

Ala Pro Leu Pro Phe Ala Tyr Asp Ile Leu Ser Thr Ser Phe Gln Tyr
    50                  55                  60

Gly Asn Arg Ala Phe Thr Lys Tyr Pro Ala Asp Ile Gln Asp Tyr Phe
65                  70                  75                  80

Lys Gln Ala Phe Pro Glu Gly Tyr His Trp Glu Arg Ser Met Thr Tyr
                85                  90                  95

Glu Asp Gln Gly Ile Cys Thr Ala Thr Ser Asn Ile Ser Met Arg Gly
            100                 105                 110

Asp Cys Phe Phe Tyr Asp Ile Arg Phe Asp Gly Thr Asn Phe Pro Pro
    115                 120                 125

Asn Gly Pro Val Met Gln Lys Lys Thr Leu Lys Trp Glu Pro Asp Thr
130                 135                 140

Glu Lys Met Tyr Val Glu Asp Gly Val Leu Lys Gly Asp Val Asn Met
145                 150                 155                 160

Arg Leu Leu Leu Glu Gly Gly His Tyr Arg Cys Asp Val Lys Thr
                165                 170                 175

Thr Tyr Lys Ala Lys Lys Glu Val Ser Leu Pro Asp Ala His Lys Ile
            180                 185                 190

Asp His Arg Ile Glu Ile Leu Glu His Asp Lys Asp Tyr Asn Lys Val
        195                 200                 205

Lys Leu Cys Glu Asn Ala Val Ala Arg Ala Ser Met Leu Pro Ser Gln
    210                 215                 220

Ala Lys
225
```

<210> SEQ ID NO 2
<211> LENGTH: 484
<212> TYPE: PRT
<213> ORGANISM: artificial sequence
<220> FEATURE:
<223> OTHER INFORMATION: Artificially Synthesized Sequence

<400> SEQUENCE: 2

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Leu Leu
            35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
    210                 215                 220

Leu Thr Ala Ala Gly Ile Thr Glu Gly Met Asn Glu Leu Tyr Lys Glu
225                 230                 235                 240

Leu Gly Gly Gly Ser Gly Gly Gly Ser Gly Gly Gly Ser
                245                 250                 255

Leu Glu Met Val Ser Val Ile Lys Pro Glu Met Lys Ile Lys Leu Cys
            260                 265                 270

Met Arg Gly Thr Val Asn Gly His Asn Phe Val Ile Glu Gly Glu Gly
        275                 280                 285

Lys Gly Asn Pro Tyr Glu Gly Thr Gln Ile Leu Asp Leu Asn Val Thr
    290                 295                 300

Glu Gly Ala Pro Leu Pro Phe Ala Tyr Asp Ile Leu Ser Thr Ser Phe
305                 310                 315                 320

Gln Tyr Gly Asn Arg Ala Phe Thr Lys Tyr Pro Ala Asp Ile Gln Asp
                325                 330                 335

Tyr Phe Lys Gln Ala Phe Pro Glu Gly Tyr His Trp Glu Arg Ser Met
            340                 345                 350

Thr Tyr Glu Asp Gln Gly Ile Cys Thr Ala Thr Ser Asn Ile Ser Met
        355                 360                 365

Arg Gly Asp Cys Phe Phe Tyr Asp Ile Arg Phe Asp Gly Thr Asn Phe
    370                 375                 380

Pro Pro Asn Gly Pro Val Met Gln Lys Lys Thr Leu Lys Trp Glu Pro
385                 390                 395                 400

Asp Thr Glu Lys Met Tyr Val Glu Asp Gly Val Leu Lys Gly Asp Val
                405                 410                 415

Asn Met Arg Leu Leu Leu Glu Gly Gly Gly His Tyr Arg Cys Asp Val
            420                 425                 430

Lys Thr Thr Tyr Lys Ala Lys Lys Glu Val Ser Leu Pro Asp Ala His
        435                 440                 445

Lys Ile Asp His Arg Ile Glu Ile Leu Glu His Asp Lys Asp Tyr Asn
    450                 455                 460

Lys Val Lys Leu Cys Glu Asn Ala Val Ala Arg Ala Ser Met Leu Pro
465                 470                 475                 480

Ser Gln Ala Lys
```

<210> SEQ ID NO 3
<211> LENGTH: 1455
<212> TYPE: DNA
<213> ORGANISM: artificial sequence
<220> FEATURE:
<223> OTHER INFORMATION: Artificially Synthesized Sequence

<400> SEQUENCE: 3

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct gctctgcacc accggcaagc tgcccgtgcc ctggcccacc     180
ctcgtgacca ccctgggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccgc cctgttcaaa gaccccaacg agaagcgcga tcacatggtc     660
ctgctggagt tcctgaccgc cgccgggatc actgaaggca tgaacgagct gtacaaggag     720
ctcggtggag gcggttcagg cggaggtggc tctggcggtg gcggatcgct cgagatggtg     780
agcgtgatca agcccgagat gaagatcaag ctgtgcatga gggcaccgt gaacggccac     840
aacttcgtga ttgagggcga gggcaagggc aacccctacg agggcaccca gatcctggac     900
ctgaacgtga ccgagggcgc ccccctgccc ttcgcctacg acatcctgtc cacctcgttc     960
cagtacggca cagggccctt caccaagtac cccgccgaca tccaggacta cttcaagcag    1020
gccttccccg agggctacca ctgggagagg agcatgacct acgaggacca gggcatctgc    1080
accgccacca gcaacatcag catgagggc gactgcttct tctacgacat caggttcgac    1140
ggcaccaact ccccccccaa cggccccgtg atgcagaaga gaccctgaa gtgggagccc    1200
gacaccgaga agatgtacgt ggaggacggc gtgctgaagg gcgacgtgaa catgaggctg    1260
ctgctggagg gcggcggcca ctacaggtgc gacgtcaaga ccacctacaa ggccaagaag    1320
gaggtgagcc tgcccgacgc ccacaagatc gaccacagga tcgagatcct ggagcacgac    1380
aaggactaca caaggtgaa gctgtgcgag aacgccgtgg ccagggcctc catgctgccc    1440
agccaggcca agtga                                                    1455
```

<210> SEQ ID NO 4
<211> LENGTH: 226
<212> TYPE: PRT
<213> ORGANISM: artificial sequence
<220> FEATURE:
<223> OTHER INFORMATION: artificial sequence

<400> SEQUENCE: 4

```
Met Val Ser Val Ile Lys Pro Glu Met Lys Ile Lys Leu Cys Met Arg
1               5                   10                  15

Gly Thr Val Asn Gly His Asn Phe Val Ile Glu Gly Glu Gly Lys Gly
            20                  25                  30

Asn Pro Tyr Glu Gly Thr Gln Ile Leu Asp Leu Asn Val Thr Glu Gly
        35                  40                  45

Ala Pro Leu Pro Phe Ala Tyr Asp Ile Leu Thr Thr Val Phe Gln Tyr
    50                  55                  60

Gly Asn Arg Ala Phe Thr Lys Tyr Pro Ala Asp Ile Gln Asp Tyr Phe
65                  70                  75                  80

Lys Gln Thr Phe Pro Glu Gly Tyr His Trp Glu Arg Ser Met Thr Tyr
                85                  90                  95
```

-continued

Glu Asp Gln Gly Ile Cys Thr Ala Thr Ser Asn Ile Ser Met Arg Gly
                100                 105                 110

Asp Cys Phe Phe Tyr Asp Ile Arg Phe Asp Gly Thr Asn Phe Pro Pro
            115                 120                 125

Asn Gly Pro Val Met Gln Lys Lys Thr Leu Lys Trp Glu Pro Asp Thr
130                 135                 140

Glu Lys Met Tyr Val Glu Asp Gly Val Leu Lys Gly Asp Val Asn Met
145                 150                 155                 160

Arg Leu Leu Leu Glu Gly Gly His Tyr Arg Cys Asp Val Lys Thr
                165                 170                 175

Thr Tyr Lys Ala Lys Lys Glu Val Arg Leu Pro Asp Ala His Lys Ile
            180                 185                 190

Asp His Arg Ile Glu Ile Leu Lys His Asp Lys Asp Tyr Asn Lys Val
                195                 200                 205

Lys Leu Tyr Glu Asn Ala Val Ala Arg Tyr Ser Met Leu Pro Ser Gln
            210                 215                 220

Ala Lys
225

<210> SEQ ID NO 5
<211> LENGTH: 15
<212> TYPE: PRT
<213> ORGANISM: artificial sequence
<220> FEATURE:
<223> OTHER INFORMATION: synthetic linker

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 22
<212> TYPE: PRT
<213> ORGANISM: artificial sequence
<220> FEATURE:
<223> OTHER INFORMATION: synthetic linker

<400> SEQUENCE: 6

Ser Gly Leu Arg Ser Ala Gly Pro Gly Thr Ser Leu Tyr Lys Lys Ala
1               5                   10                  15

Gly Phe Pro Val Ala Thr
            20

<210> SEQ ID NO 7
<211> LENGTH: 33
<212> TYPE: PRT
<213> ORGANISM: Homo sapiens

<400> SEQUENCE: 7

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Pro Pro Glu
            20                  25                  30

Gly

<210> SEQ ID NO 8
<211> LENGTH: 16
<212> TYPE: PRT
<213> ORGANISM: Saccharomyces cerevisiae

```
<400> SEQUENCE: 8

Ala Cys Lys Asn Trp Phe Ser Ser Leu Ser His Phe Val Ile His Leu
1               5                   10                  15

<210> SEQ ID NO 9
<211> LENGTH: 54
<212> TYPE: PRT
<213> ORGANISM: Mus musculus

<400> SEQUENCE: 9

Pro Arg Ser Arg Pro Met Trp Gln Leu Met Lys Gln Ile Gln Ser His
1               5                   10                  15

Gly Phe Pro Pro Glu Val Glu Glu Gln Asp Asp Gly Thr Leu Pro Met
            20                  25                  30

Ser Cys Ala Gln Glu Ser Gly Met Asp Arg His Pro Ala Ala Cys Ala
        35                  40                  45

Ser Ala Arg Ile Asn Val
        50
```

PH-RESPONSIVE PROTEOLYSIS PROBE

TECHNICAL FIELD

The present invention relates to a probe for quantifying autophagy, the probe having a fluorescent protein.

BACKGROUND ART

Autophagy is a process of degrading various cellular components ubiquitously observed in eucaryocytes. Autophagy is mainly classified into macrophagy, microautophagy, and chaperone-mediated autophagy, based on the mechanisms of occurrence of the autophagy. In any mechanism, the components are ultimately translocated into lysosomes or vacuoles and degraded by degrading enzymes existing inside the lysosomes or the vacuoles. Organelles such as mitochondria and endoplasmic reticulums, as well as biological molecules such as proteins, are degraded by autophagy. Autophagy which degrades mitochondria is also called mitophagy.

Autophagy is induced, for example, by depletion in nutrients. Accordingly, supply of nutrients to cells via recycling of degradation products of components in the cytoplasm had been considered to be a main role of autophagy. However, autophagy has recently been found to be associated with various vital phenomena, such as quality control of proteins or organelles, bacterial infection, antigen presentation, cell death, canceration, and embryogenesis. It is also suggested that autophagy is associated with degradation and elimination of abnormal proteins that accumulate and aggregate in cells. Furthermore, it is suggested that autophagy is associated with neurodegenerative diseases (e.g., Huntington's disease or Alzheimer's disease) which are considered to develop due to cell death caused by accumulation of abnormal proteins (Deretic, V. and Klionsky, D. J., Scientific American, Vol. 298, pp. 74-81, 2008). As such, it is highly necessary to develop a simple and accurate method for quantifying the activity of autophagy with the aim of elucidating mechanisms of the vital phenomena and developing methods for treating diseases associated with autophagy.

In the past, autophagy had been measured by: observing cells under electron microscope; detecting degradation of a radioisotope-labeled protein; measuring an activity of a modified enzyme designed to be activated specifically upon autophagy; or other techniques. However, such techniques had insufficient specificity for autophagy, or involved procedures so complicated as to require skills and times.

In macroautophagy, a portion of cytoplasm is wrapped with a membrane called separation membrane at first, thereby forming a vesicle called autophagosome (having a diameter of about 1 μm). Then, the autophagosome is fused to a lysosome, whereby the incorporated components of the cytoplasm are then degraded. Among autophagy-related proteins that have heretofore been reported, a protein related to autophagosome formation and localized in the membrane, such as LC3, is known. On the basis of this knowledge, a fusion protein of such protein and a fluorescent protein is expressed in cells, and autophagy is measured by monitoring the accumulation of the fusion protein in the vesicular structure or the decrease in fluorescence intensity caused by degradation in the lysosome (Mizushima, N., Int. J. Biochem. Cell Biol., Vol. 36, pp. 2491-2502, 2004; and Shvets, E. et al., Autophagy, Vol. 4, pp. 621-628, 2008).

However, the formation of autophagosome is a phenomenon observed only in the case of macroautophagy. As such, it is impossible to detect microautophagy or chaperone-mediated autophagy by the method as mentioned above. In the case of microautophagy or chaperone-mediated autophagy, vesicles for transfer, such as autophagosome, are not formed, and components of the cytoplasm are thought to be directly incorporated into the lysosome. At present, however, research on microautophagy and chaperone-mediated autophagy has not advanced as that of macroautophagy, and there are no effective methods for measurement in the research. It is thus impossible to determine the total of activities of all types of autophagy occurring in cells.

While the pH in the cytoplasm is neutral (pH, around 7), the pH in the lysosome or vacuole in which components of the cytoplasm are degraded by autophagy is acidic (pH, around 4). There is a method that, through utilizing such pH properties, the activity of autophagy can be measured based on pH-dependent changes in fluorescent properties caused by transfer of a fluorescent probe reagent resistant to degrading enzymes to the lysosome or vacuole. Because components of the cytoplasm are ultimately incorporated into the lysosome or vacuole in all types of autophagy, the total of autophagy activities can be measured by this method.

Examples of the method include Rosado et al. (Non-patent Literature 1), which uses a probe produced by ligating, via a linker peptide, DsRed.T3 to super ecliptic pHluorin. DsRed.T3 is a fluorescent protein that emits red fluorescence (587 nm) at a relatively constant level of intensity independent of pH changes in the environment. The super ecliptic pHluorin is a fluorescent protein that emits green fluorescence (508 nm) that exhibits lowered fluorescence intensity as pH becomes more acidic. In Non-patent Literature 1, such probe is expressed in the cytoplasm, and then pH changes that occur when the probe is incorporated into the lysosome together with other components of the cytoplasm are measured as changes in a ratio of intensities of two fluorescences having different colors, thereby determining the activity of autophagy.

CITATION LIST

Non-Patent Literature

[Non-Patent Literature 1]
Rosado, C. J. et al., Autophagy, Vol. 4, p. 205-213, 2008

SUMMARY OF INVENTION

Technical Problem

In reality, it is difficult to perform the accurate measurement of autophagy activity with use of Rosella described in Non-patent Literature 1. Rosella has the following problems.

Firstly, yeast, autophagy in which is observed in Non-patent Literature 1, has vacuoles that are not significantly acidic (pH, around 5.5 to 6.0). Meanwhile, mammalian cells have lysosomes that are more acidic environments (pH, around 4.0 to 5.0) as compared to yeast. Both of the two fluorescent proteins constituting Rosella have a property of being weak against an acidic condition and acidic protease. This results in irreversible quenching or degradation of the fluorescent proteins under a condition corresponding to mammalian cells. Secondly, in detection of autophagy in a mammalian cell, due to a difference between pH-independent fluorescence properties of the two fluorescent proteins in terms of quenching properties caused by the folding speed or photobleaching in cells, the value of the ratio may probably vary depending on experimental conditions. Thirdly, because changes in the ratio depend only on fluorescence changes of the super ecliptic pHluorin, the magnitudes of changes observed are small.

Keima, which is used in an autophagy measuring method previously developed by the inventors of the present invention, has a property of being strong also in an acidic environment. However, a fluorescent signal of Keima reversibly changes in accordance with pH. This feature causes a problem in autophagy detection in such cases where, for example, a living cell is fixed to be used as a specimen. In the case of fixing a living cell as a specimen, pH in the cell changes in accordance with a change in an ambient environment. This change in pH causes the fluorescent signal of keima to change as compared with a fluorescent signal of keima in a state where the cell was a living cell. This prevents accurate measurement of autophagy.

Under these circumstances, in order to perform accurate quantification of autophagy activity, there are needs for an excellent tool that has both (i) a property of emitting a stable fluorescent signal even in an environment with pH that is equivalent to pH inside a lysosome or a vacuole of a mammalian cell and (ii) a property of not experiencing any influence, on a fluorescent signal indicative of autophagy, from a pH change resulting from a change in an ambient environment.

Solution to Problem

In designing a probe of a pH-responsive fluorescent protein, the inventors of the present invention have paid attention to utilizing a difference between protease sensitivities of fluorescent proteins under an acidic condition. The inventors have developed an idea that accurate autophagy detection would be possible both in a living cell and in a fixed cell by utilizing the difference between the protease sensitivities, instead of a difference (as in the case of the probe disclosed in Non-patent Literature 1) between pH sensitivities of chromophores from fluorescent proteins. Based on the idea, the inventors have found that the foregoing problems can be solved by a FRET probe which is produced by combining fluorescent proteins that significantly differ in protease sensitivity under an acidic condition. As a result, the inventors have completed the present invention. That is, the present invention has the following features.

(1) A unimolecular FRET probe, including: an acceptor consisting of a fluorescent protein to be enzymatically degraded in a lysosome or a vacuole; and a donor having an amino acid sequence having a sequence identity of 95% or more with respect to an amino acid sequence represented by SEQ ID NO: 1.

(2) The unimolecular FRET probe as set forth in (1), wherein the fluorescent protein is a yellow fluorescent protein derived from *Aequorea victoria*.

(3) The unimolecular FRET probe as set forth in (1) or (2), wherein the fluorescent protein is selected from the group consisting of YFP, EYFP, Ypet, Topaz, Citrine, mCitrine, mEYFP, Venus, mVenus, and TagYFP.

(4) The unimolecular FRET probe as set forth in any one of (1) through (3), further including a mitochondrial localization sequence.

(5) A polynucleotide encoding a unimolecular FRET probe recited in any one of (1) through (4).

(6) A kit including a polynucleotide recited in (5).

(7) A method for quantifying an activity of autophagy, including detecting a fluorescent signal from a cell containing a unimolecular FRET probe recited in any one of (1) through (3).

(8) The method as set forth in (7), wherein the cell has been fixed.

Advantageous Effects of Invention

The present invention allows providing a tool having an excellent property which, in quantification of an activity of autophagy, allows highly accurate analysis without being affected by a fluctuation in pH inside a lysosome or a vacuole.

BRIEF DESCRIPTION OF DRAWINGS

FIG. 9 is a view schematically illustrating arrangements of a conventional probe and a probe in accordance with an example of the present invention, each of the probes including a mitochondrial localization sequence.

DESCRIPTION OF EMBODIMENTS

[Unimolecular FRET Probe (pH-Responsive Proteolysis Probe)]

Figure 1:
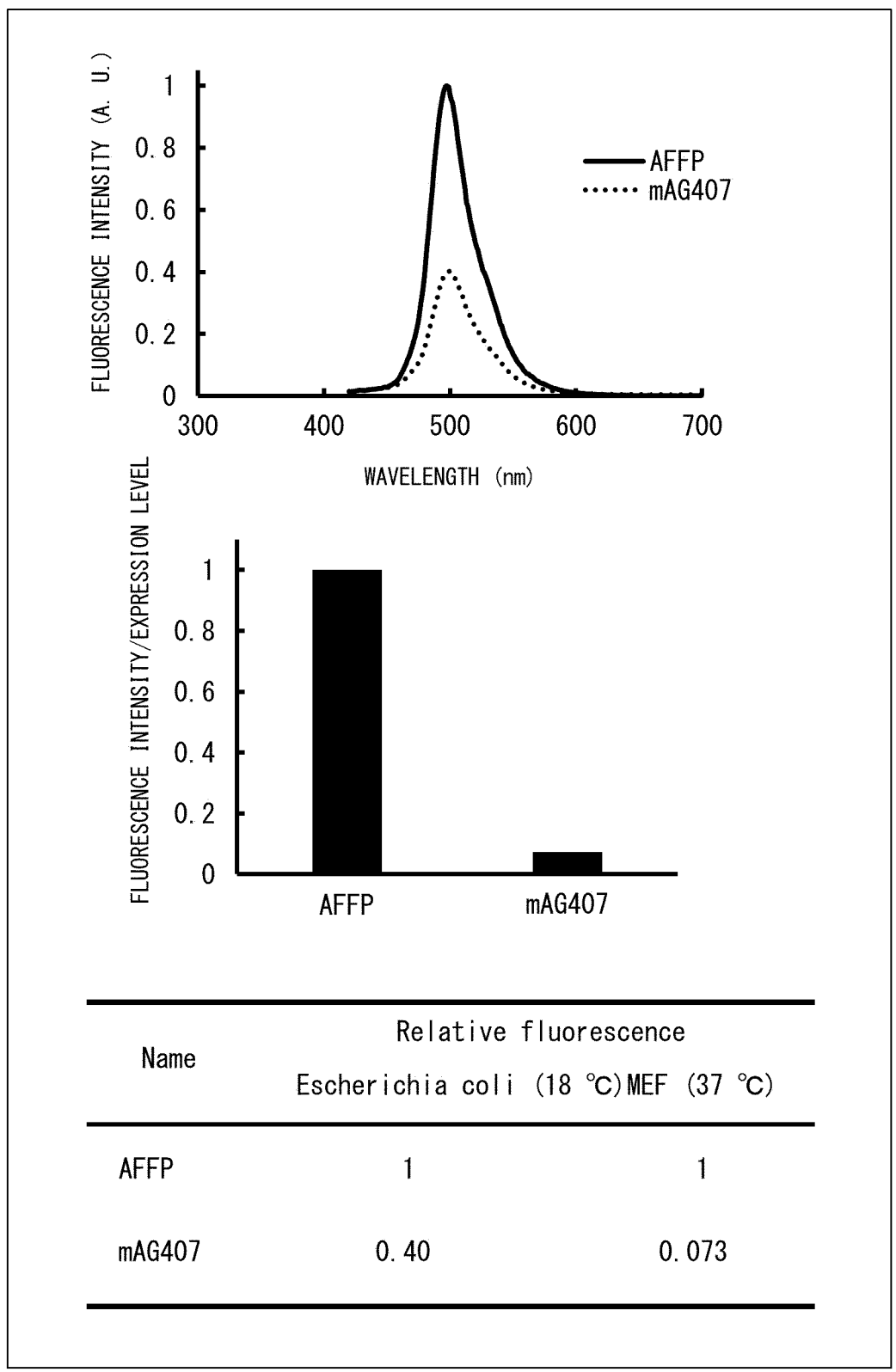
FIG. 1 is a view showing a result from comparison between fluorescence intensity of a fluorescent protein expressed in *Escherichia coli* (18° C.) and that of a fluorescent protein expressed in mammalian cells (MEF cells, 37° C.).

A unimolecular FRET probe of the present invention includes: an acceptor consisting of a fluorescent protein to be enzymatically degraded inside a lysosome or a vacuole; and a donor having an amino acid sequence having a sequence identity of 95% or more with respect to an amino acid sequence represented by SEQ ID NO: 1.

The acceptor and the donor are fluorescent proteins which emit respective different fluorescence in a case where each of the acceptor and the donor exists as a single protein. The acceptor existing as a single protein emits fluorescence with a first wavelength in a state where the acceptor is excited. The donor existing as a single protein emits fluorescence with a second wavelength in a state where the donor is excited. The first wavelength is longer than the second wavelength which is within a wavelength range corresponding to a green color.

Accordingly, when the unimolecular FRET probe is present in a cytoplasm (i.e., under a neutral pH condition), both of the donor and the acceptor can emit fluorescence. However, since the donor being excited provides energy to the acceptor, the unimolecular FRET probe mainly emits fluorescence with the first wavelength, and weakly emits fluorescence with the second wavelength. At this time, a signal (referred to as a negative signal) which is emitted from the unimolecular FRET probe and mainly consists of the fluorescence with the first wavelength is not associated with autophagy.

When the unimolecular FRET probe transfers from the cytoplasm into a lysosome or a vacuole (i.e., under an acidic pH condition), the portion (including the acceptor) other than the donor is degraded, so that the unimolecular FRET probe irreversibly transforms into a structure in which the donor remains. This is because, as described later, a fluorescent protein that exhibits resistance to degradation by acidic protease is specifically selected as the donor in accordance with the present invention. Accordingly, fluorescence emitted from inside the lysosome or the vacuole is only fluorescence with the second wavelength, since only the donor is present inside the lysosome or the vacuole. This signal (referred to as a positive signal), which consists only of the fluorescence with the second wavelength, indicates autophagy.

As described above, the unimolecular FRET probe (or a part thereof) in accordance with the present invention emits a negative signal or a positive signal in a pH-dependent manner. Note that this change in signal of the unimolecular FRET probe is irreversible, and the mechanism of the change is clearly different from a conventional mechanism which utilizes a difference between pH sensitivities of two chromophores from fluorescent proteins. In the conventional mechanism, a pH-dependent reversible change occurs in a fluorescence property obtained by combining fluorescence emissions from the respective two chromophores in the entire molecule. Meanwhile, the unimolecular FRET probe in accordance with the present invention emits a negative signal when the entire molecule is maintained (i.e., under a neutral condition), and emits a positive signal when the acceptor is degraded (i.e., in response to a low pH) under an acidic condition. Since the acceptor once degraded will not be regenerated, the donor keeps emitting a positive signal even after an acidic pH of the ambient environment has increased to become neutral. That is, the unimolecular FRET probe in accordance with the present invention undergoes an irreversible change in signal only in response to a pH decrease (neutral to acidic), and is insensitive to a pH increase. In contrast, a probe based on the conventional mechanism undergoes a reversible change in signal in response to pH changes (neutral to acidic, and acidic to neutral).

Thus, the donor remaining in the lysosome or the vacuole after the degradation of the acceptor emits only a positive signal and does not emit a negative signal, even when the pH of the ambient environment has changed to pH other than acidic pH. Accordingly, with use of the unimolecular FRET probe in accordance with the present invention, the total of positive signals indicative of autophagy is successfully detected without undergoing a change, even in a case where, for example, the pH changes from acidic to neutral due to an elapse of time after occurrence of cell death.

Further, in a case where the unimolecular FRET probe in accordance with the present invention is used, fluorescence constituting the negative signal and fluorescence constituting the positive signal have respective different main components. More specifically, a fluorescent component with the first wavelength, which component is dominant in a negative signal under a neutral condition, is lost in an acidic condition. On the other hand, there is a dramatic change of a fluorescent component with the second wavelength, which component is weakly present in a negative signal, into the only fluorescent component in a positive signal under an acidic condition. As such, the use of the unimolecular FRET probe in accordance with the present invention allows autophagy activity to be easily quantified on the basis of whether or not a fluorescent component with the second wavelength is substantially present.

Thus, it is possible to perform very accurate quantification of autophagy activity in a cell which has been fixed after introduction of the unimolecular FRET probe into the cell. The unimolecular FRET probe has excellent properties of both (i) eliminating the trouble of handling living cells and (ii) enabling an improvement in accuracy of analysis.

(Autophagy)

Autophagy is a process in which a cell degrades its own components, such as proteins or organelles (e.g., mitochondria or endoplasmic reticulum). Autophagy is mainly classified into macrophagy, microautophagy, and chaperone-mediated autophagy, based on the mechanisms of occurrence of the autophagy.

The term "autophagy activity" used herein refers to the capacity for clearance (cleaning) in cells. When autophagy activity is high, the clearance is regarded as functioning sufficiently in living cells. When autophagy normally progresses, cellular homeostasis is considered to be maintained.

In macroautophagy, when cells receive a stress (e.g., nutrient starvation, excessive protein production, or accumulation of abnormal proteins), proteins related to the stress or organelles and phospholipid are accumulated, so that autophagosome is formed. In animal cells, the autophagosome undergoes membrane fusion with the intracellular lysosome to form an autolysosome. In yeast or plant cells, the autophagosome undergoes membrane fusion with the vacuole. As a result, the components above are degraded by proteolytic enzymes existing in lysosomes or vacuoles. The above series of processes of degrading the components is called macroautophagy.

Microautophagy is a process in which components (e.g., excessively produced proteins or abnormal proteins) are directly incorporated into lysosomes or vacuoles without undergoing the above-described membrane fusion and then degraded therein.

Chaperone-mediated autophagy is a process in which components (e.g. excessively produced proteins or abnormal proteins) are incorporated into lysosomes or vacuoles through a binding of chaperone to the components.

In any mechanism, the components are ultimately incorporated into lysosomes or vacuoles, and are degraded by degrading enzymes existing in the lysosomes or the vacuoles. Organelles such as mitochondria and endoplasmic reticulums, as well as biological molecules such as proteins, are degraded by autophagy. Autophagy which degrades mitochondria is also called mitophagy. It is suggested that autophagy is associated with a great variety of vital phenomena. As such, facilitating and simplifying the quantification of autophagy activity has an enormous potential for elucidating various vital phenomena.

Next, the following description will describe details of components of the unimolecular FRET probe.

(Donor)

The donor has high resistance to degradation by acidic protease, high fluorescence intensity, and stability of the fluorescence intensity under an acidic condition. In order to emit a positive signal under an acidic condition, it is essential that the donor have high resistance to degradation by acidic protease. Further, in order to maximize the value of a ratio of the positive signal to a negative signal, the donor is required to have high fluorescence intensity and stability of the fluorescence intensity in an acidic condition. Details of such a donor in accordance with the present invention will be described below.

The donor has an amino acid sequence having a sequence identity of 95% or more with respect to an amino acid sequence represented by SEQ ID NO: 1. According to this arrangement, the second fluorescence emitted from the donor has high fluorescence intensity and does not undergo a decrease in intensity under an acidic condition. The donor has an amino acid sequence having a sequence identity of preferably 96% or more, more preferably 97% or more, further more preferably 98% or more, and most preferably 99% or more with respect to the amino acid sequence represented by SEQ ID NO: 1.

In other words, from a point of view other than sequence identity, the donor has an amino acid sequence with a substitution, addition, deletion, and/or insertion of 11 or less amino acid residues in the amino acid sequence represented by SEQ ID NO: 1. Accordingly, the donor has an amino acid sequence with a substitution, addition, deletion, and/or insertion of preferably 10 or less, more preferably 8 or less, and further more preferably several (5 to 6, preferably 2 to 3) or less amino acid residues in the amino acid sequence represented by SEQ ID NO: 1. Details of the amino acid sequence of the donor will be described below.

The donor has, for example, an amino acid sequence represented by SEQ ID NO: 1 as described in the Examples. As described above, however, the amino acid sequence of the donor is allowed to be changed within a certain range. For example, the amino acid sequence of the donor is allowed to be changed provided that the amino acid sequence thus changed has (i) resistance to degradation by acidic protease, (ii) fluorescence intensity, and (iii) stability of the fluorescence intensity at levels substantially equal to or higher than those of a donor having the amino acid sequence represented by SEQ ID NO: 1.

The amino acid substitution herein may be conservative substitution or non-conservative substitution of an amino acid. The conservative substitution of an amino acid may be carried out in accordance with physical or chemical properties (e.g., an electrical property, a structural property, a hydrophobic property, and polarity). Examples of a group of amino acids sharing such properties may include a hydrophobic amino acid, a polar amino acid, an acidic amino acid, a basic amino acid, and an aromatic amino acid. Examples of the hydrophobic amino acid include glycine, isoleucine, leucine, alanine, methionine, and proline. Examples of the polar amino acid include asparagine, glutamine, threonine, serine, tyrosine, and cysteine. Examples of the acidic amino acid include asparagine acid and glutamine acid. Examples of the basic amino acid include arginine, lysine, and histidine. Examples of the aromatic amino acid include phenylalanine, tyrosine, tryptophan, and histidine.

Examples of a portion of the amino acid sequence of the donor in which portion a change of an amino acid is preferably avoided may include Q62, Y63, G64, S58, S60, A82, D142, V173, E182, S184, E199, C210, and A217, when the amino acids are counted from the second position of SEQ ID NO: 1.

Accordingly, (i) the amino acid sequence of the donor has one or more, preferably three or more, and more preferably five or more of Q62, Y63, G64, S58, S60, A82, D142, V173, E182, S184, E199, C210, and A217 or (ii) a change of an amino acid at each of these amino acid positions is conservative substitution.

When irradiated with excitation light, the donor emits green fluorescence with a peak wavelength of 450 nm to 510 nm. The peak wavelength may be changed as appropriate within the above range in accordance with a peak wavelength of the acceptor (described later).

As described above, the donor has high resistance to degradation in lysosomes or vacuoles of living cells. More specifically, in an acidic condition (pH 3 to 6, preferably pH 4 to 6), the donor has resistance to degradation by acidic protease existing in lysosomes or vacuoles.

Note that the donor is a donor in the FRET probe. That is, the donor is a fluorescent protein which, when in proximity to the acceptor (described later), provides the acceptor with energy which the donor has obtained by being irradiated with excitation light. The acceptor which has received the energy from the donor emits fluorescence. Accordingly, the fluorescence which the donor emits by being irradiated with the excitation light has a wavelength shorter than that of fluorescence which the acceptor emits by receiving the energy from the donor.

(Acceptor)

As described above, the acceptor is a fluorescent protein which is enzymatically degraded in a lysosome or a vacuole. As such, the acceptor may be referred to also as a fluorescent protein which is more likely to be enzymatically degraded inside a lysosome or a vacuole than the donor is. When the unimolecular FRET probe is transported into a lysosome or a vacuole, the acceptor is enzymatically degraded. Out of the unimolecular FRET probe, it is the donor which remains after the degradation by the enzyme. Accordingly, when the unimolecular FRET probe is transported into a lysosome or a vacuole, fluorescence with the first wavelength which is based on the acceptor is lost. As a result, the donor emits only fluorescence with the second wavelength which is caused by excitation of the donor. In accordance with such a mechanism, the unimolecular FRET probe exhibits an action as described above.

Since the acceptor is excited by fluorescence emitted from the donor, a part of an excitation wavelength of the acceptor overlaps with a fluorescence wavelength of the donor. The excitation wavelength of the acceptor is within a range of preferably not lower than 430 nm but not higher than 530 nm, more preferably not lower than 450 nm but not higher than 510 nm, at pH 4 to pH 9. An excitation peak wavelength of the acceptor is within a range of preferably not lower than 440 nm but not higher than 520 nm, more preferably not lower than 450 nm but not higher than 510 nm.

The acceptor has a fluorescence peak wavelength which at least is longer than a fluorescence peak wavelength of the donor. The difference in fluorescence peak wavelength between the acceptor and the donor is preferably not less than 20 nm, more preferably not less than 30 nm, further more preferably not less than 40 nm, at pH 4 to pH 9. The greater the difference, the easier it becomes to distinguish between a fluorescent signal emitted by the unimolecular FRET probe (before degradation of the acceptor) and a fluorescent signal emitted by a remaining probe (after the degradation of the acceptor).

The acceptor is preferably a fluorescent protein which is derived from *Aequorea victoria*, a jellyfish, and which emits a yellow fluorescence, an orange fluorescence, or a red fluorescence. More preferably, the acceptor is a yellow fluorescent protein derived from *Aequorea victoria*.

The "yellow fluorescent protein derived from *Aequorea victoria*" used herein refers to (i) a fluorescent protein which is produced as a result of genetic modification of GFP (Green Fluorescent Protein), which is a fluorescent protein isolated from *Aequorea victoria* or (ii) a fluorescent protein which is produced as a result of genetic modification of TagGFP, which is a fluorescent protein isolated from *Aequorea macrodactyla*. Examples of the "fluorescent protein which is produced as a result of genetic modification of GFP" may include, but are not limited to, YFP, EYFP, Ypet, Topaz, Citrine, mCitrine, mEYFP, Venus, and mVenus, and can further include a modified fluorescent protein which is produced by modification (deletion, substitution, insertion, and/or addition) of a part of amino acids of such a fluorescent protein and which maintains a yellow fluorescence characteristic. Examples of the "fluorescent protein which is produced as a result of genetic modification of TagGFP" may include, but are not limited to, TagYFP, and can further include a modified fluorescent protein which is produced by modification (deletion, substitution, insertion, and/or addition) of a part of amino acids of TagYFP and which maintains a yellow fluorescence characteristic. Examples of the "modified fluorescent protein which is produced by modification (deletion, substitution, insertion, and/or addition) of a part of amino acids" may include a fluorescent protein which maintains a sequence identity of preferably not less than 90%, more preferably not less than 95%, with respect to the fluorescent protein before the modification.

The acceptor does not necessarily have to be a fluorescent protein derived from *Aequorea victoria*. In this case, the acceptor is preferably a fluorescent protein which undergoes irreversible quenching or enzyme degradation inside a lysosome or a vacuole through an introduction of mutation or the like.

(Linker)

The unimolecular FRET probe in accordance with the present invention may include a linker as necessary. The linker is a peptide sequence which consists of one or more amino acid residues and links the acceptor to the donor. The linker has a length within a range of preferably 2 amino acid residues to 100 amino acid residues, more preferably 2 amino acid residues to 50 amino acid residues.

One of the roles of the linker is to locate the acceptor and the donor so as to increase an effect of the FRET as compared with a case without the linker (a case in which the acceptor and the donor are directly fused). Accordingly, it is preferable that the linker have a low or substantially no cytotoxicity, and have little or substantially no influence on light-emitting characteristics of the acceptor and the donor. As long as the linker corresponds to such a linker, the amino acid sequence of the linker is not particularly limited.

(Subject to be Analyzed for Autophagy)

The unimolecular FRET probe may include given a biological molecule which is degraded inside a lysosome or a vacuole. The biological molecule may be a molecule which is known or expected to be associated with autophagy activity, or a molecule whose association with autophagy activity has not been suggested in the past. The biological molecule is preferably a protein, since, as described later, autophagy activity can be measured with use of a polynucleotide or a kit including the polynucleotide.

(Mitochondrial Localization Sequence)

The unimolecular FRET probe may further include a mitochondrial localization sequence. A probe containing a mitochondrial localization sequence mainly accumulates in mitochondria, instead of being localized uniformly throughout inside the cell. Accordingly, the use of the probe allows quantifying specific degradation of mitochondria by lysosomes or vacuoles.

Examples of the mitochondrial localization sequence may include a CoxVIII sequence. These example sequences may be introduced into the unimolecular FRET probe in such a manner that (i) one or more of one type of the example sequences, (ii) two or more of one type of the example sequences (the one type is repeated), (iii) one or more of each of more than one type of the example sequences, or (iv) three or more sequences (which are made up of more than one type of the example sequences and include a repetition of a type of the example sequences) is/are introduced.

(Other Sequences)

Instead of the mitochondrial localization sequence, the unimolecular FRET probe may include another localization sequence or a signal sequence. Examples of the another localization sequence or the signal sequence may include a vacuole localization sequence, a nuclear localization signal sequence, and a localization signal sequence for localization to an organelle other than a lysosome, a vacuole, and a nucleus. Introduction of such a sequence into the unimolecular FRET probe allows maturing of nucleated cells into denucleated cells to be quantified through, for example, quantification of specific autophagy in nuclei.

Examples of the lysosome localization sequence may include cathepsin D. Examples of the nuclear localization signal sequence may include an NLS derived from c-myc. Examples of the organelle other than a lysosome, a vacuole, and a nucleus may include a peroxisome localization SKL motif and the like.

In combination with the localization sequence above of various kinds and the signal sequence above, the unimolecular FRET probe may include a sequence of various kinds, examples of which may include, in addition to the mitochondrial localization sequence, a CL1 sequence and a PEST sequence as degron sequences for eliminating a delocalization probe remaining in the cytoplasm.

[Polynucleotide]

A polynucleotide in accordance with the present invention encodes the unimolecular FRET probe. Accordingly, introducing the polynucleotide into a cell to be analyzed for various types of autophagy allows the unimolecular FRET probe to be expressed in the cell.

The polynucleotide in accordance with the present invention may exist in the form of an RNA (e.g., mRNA) or in the form of a DNA (e.g., cDNA). The DNA may be double-stranded or single-stranded. The polynucleotide in accordance with the present invention may be a polynucleotide that includes only a sequence of an ORF (open reading frame), and may be a polynucleotide further including a sequence of an untranslated region (UTR).

Further, the polynucleotide in accordance with the present invention is obtained by adding, to the aforementioned polynucleotide as necessary, a polynucleotide encoding a tag sequence such as a His, HA, Myc, or Flag tag sequence. The polynucleotide in accordance with the present invention is obtained by adding, to the aforementioned polynucleotide as necessary, a polynucleotide encoding the linker.

The polynucleotide in accordance with the present invention may be produced by linearly ligating a plurality of polynucleotides encoding polypeptides of components such as the donor, the acceptor, and the linker or the tag sequence which is used as necessary. The ligation of the plurality of polynucleotides may be performed, for example, in accordance with a genetically engineered method or a nucleic acid synthesis method.

In one embodiment, the polynucleotide in accordance with the present invention is a polynucleotide whose base sequence is represented by SEQ ID NO: 3 and which encodes a FRET probe whose amino acid sequence is represented by SEQ ID NO: 2.

The polynucleotide in accordance with the present invention allows expressing a fusion protein encoded by the polynucleotide in a cell, for example, in accordance with the following procedure. The polynucleotide is subcloned to an expression vector or the like, so that an expression construct for expressing the fusion protein, which is the unimolecular FRET probe, is produced. Subsequently, the expression construct is introduced into a cell, so that the fusion protein encoded by the polynucleotide is expressed in the cell.

[Vector and Expression Construct]

(Expression Construct)

The present invention provides an expression construct which is used for producing the unimolecular FRET probe in accordance with the present invention. The term "expression construct" refers to an expression unit which includes (i) an expression regulatory region functional in an expression host and (ii) a polynucleotide operably ligated to the expression regulatory region. An example of the expression construct is a nucleic-acid construct obtained by ligating the above expression regulatory region to the above polynucleotide in a genetically engineered manner. The term "operably ligated" refers to a state in which the expression of a polynucleotide is controlled with use of an expression regulatory sequence. The expression construct may be in the form of an expression vector. The expression vector may be (i) a vector for expressing the unimolecular FRET probe in a host cell or (ii) a vector used for producing the unimolecular FRET probe in vitro.

In an expression vector, elements necessary for transcription (e.g., a promoter sequence, etc.) (equivalent to the "expression regulatory region") are operably ligated to the nucleotide in accordance with the present invention. The promoter sequence is a DNA sequence which shows a transcriptional activity in host cells. The type of a promoter sequence used is appropriately selected depending on the type of host cells and the purpose of using the unimolecular FRET probe in accordance with the present invention.

Examples of a promoter sequence which is functional in host cells may include a *Bacillus stearothermophilus* maltogenic amylase gene promoter, a *Bacillus licheniformis* alpha-amylase gene promoter, a *Bacillus amyloliquefaciens* BAN amylase gene promoter, a *Bacillus subtilis* alkaline protease gene promoter, a *Bacillus pumilus* xylosidase gene promoter; a PR promoter or a PL promoter of phage rhamda; a lac promoter, a trp promoter, and a tac promoter of *Escherichia coli*; a polyhedrin promoter, a P10 promoter, an *Autographa californica* polyhedrosis basic protein promoter, a baculovirus immediate-early gene 1 promoter, a baculovirus 39K delayed-early gene promoter, promoters derived from yeast glycolytic genes, an alcohol dehydrogenase gene promoter, a TPI1 promoter, an ADH2-4c promoter, an ADH3 promoter, a tpiA promoter, a Cauliflower mosaic virus 35S promoter, an SV40 promoter, an MT-1 (metallothionein gene) promoter, a cytomegalo promoter, and an adenovirus-2 major late promoter.

In the expression vector, the polynucleotide in accordance with the present invention may be functionally ligated to an appropriate terminator (e.g., a polyadenylation signal, a mammalian growth hormone terminator, a TPI1 terminator, or an ADH3 terminator), as necessary. The type of the appropriate terminator is appropriately selected depending on the type of host cells.

The expression vector may further have elements such as a transcription enhancer sequence or a translation enhancer sequence. The expression vector may further include a DNA sequence which enables the replication of the expression vector in host cells. SV40 replication origin is an example of the DNA sequence when the host cells are mammalian cells.

(Vector)

The polynucleotide in accordance with the present invention can be inserted into a suitable vector and used. The type of the vector is either a vector that can autonomously replicate (e.g., a plasmid, etc.), or a vector that is integrated into the genomes of host cells when it is introduced into the host cells and is then replicated together with the chromosome of the host cells. Note that the term "vector" when simply used encompasses not only the above expression vector but also, for example, a vector for cloning, and the like.

The vector may further include a selective marker. Examples of such a selective marker may include drug resistant genes against a drug such as ampicillin, kanamycin, tetracycline, chloramphenicol, neomycin or hygromycin. Use of the selective marker allows confirming: whether or not the polynucleotide in accordance with the present invention has been introduced into a host cell; whether or not the polynucleotide is actually expressed in the host cell; and the like.

[Kit]

The present invention provides a kit which includes the polynucleotide in accordance with the present invention. In addition to the polynucleotide in accordance with the present invention, the kit may further include at least one selected from (i) a vector into which the polynucleotide is to be inserted, (ii) a host cell to be transformed with use of the vector, and (iii) the like. Further, in the kit in accordance with the present invention, the polynucleotide in accordance with the present invention may be included as a vector in which the polynucleotide has been inserted, or a transformant including the polynucleotide.

The kit is a kit for utilizing the unimolecular FRET probe in accordance with the present invention, and may be, for example, a kit for measuring autophagy activity, or a kit for screening for a compound which affects autophagy activity. Accordingly, the kit may include (i) a reagent used for measuring autophagy activity or for screening for a compound which affects the autophagy activity, (ii) a compound to be used as a control, or (iii) the like. The kit in accordance with the present invention may include an instruction manual for the kit. The instruction manual of the kit explains procedures of various methods (described later) and may be in the form of visiting a website which presents the procedures of the methods. The instruction manual of the kit may be provided in the form of a printed paper medium or a computer-readable recording medium.

[Generation of Transformant]

Introducing a vector into cells (i.e., transformation) can be conducted by techniques such as the calcium phosphate, lipofection and electroporation methods.

A recombinant protein expressed through the culture of cells can be collected and/or purified from the cells or from extracellular fluid (when a signal peptide is used) by techniques, such as cell wall destruction, ammonium sulfate, ethanol precipitation, acid extraction, anion or cation exchange chromatography, hydrophobic interaction chromatography, affinity chromatography, and HPLC.

In the present invention, the unimolecular FRET probe or a vector including DNA encoding the same is used in order to measure (quantify) cellular autophagy (the activity or occurrence thereof). Since the cells used herein are eucaryocytes (e.g., fungal cells (such as yeast, filamentous fungi, or basidiomycetes), plant cells, or animal cells (such as insect cells or mammalian cells)) in particular, vectors (e.g., plasmid, phage, cosmid, or virus vectors) suitable for such cells are used.

Examples of vectors suitable for yeast cells may include pG-1, YEp13, YCp50, pGBT9, pGAD424, and pACT2 vectors (manufactured by Clontech). Examples of vectors suitable for plant cells may include pBI and T-DNA vectors. Examples of vectors suitable for animal cells may include pRc/RSV, pEF6/Myc-His, pRc/CMV (e.g., Invitrogen), bovine papilloma virus plasmid (pBPV) (Amersham Pharmacia Biotech), EB virus plasmid (pCEP4) (Invitrogen), and insect virus vectors, such as baculovirus vectors.

Introducing a vector into cells (i.e., transformation or transfection) can be conducted by well-known techniques in the field. Examples of such techniques may include calcium phosphate, DEAE dextran, lipofection, electroporation, microinjection, liposomes, *Agrobacterium*, gene gun, viral infection, spheroplast or protoplast methods.

When the unimolecular FRET probe is directly introduced into a cell, alternatively, the unimolecular FRET probe may be bound to a membrane-permeable peptide or encapsulated into a liposome, in order to introduce the probe into a cell.

[Utilization of Unimolecular FRET Probe]

(Method for Quantifying Autophagy)

A quantification method for quantifying an activity of autophagy with use of the unimolecular FRET probe includes detecting a fluorescent signal from a cell. As described above, the use of the unimolecular FRET probe enables easy and simple quantification of autophagy activities in cells on the basis of a fluorescent signal detected. Details of the method will be described below with reference to specific examples. Note that descriptions in this item correspond to an embodiment in which the subject described in the item "(Subject to be analyzed for autophagy)" is included in the unimolecular FRET probe.

The cell may be present in a given form in a sample. The given form may be, for example, a cultured living cell, a fixed dead cell, a living cell or a fixed dead cell each of which is present in a tissue, or a living cell or a fixed dead cell each of which is present in an individual. As described above, according to the method, a signal indicative of autophagy activity does not attenuate even in a case where a cell death occurs after introduction of the probe. Accordingly, autophagy activity can be quantified regardless of whether or not the cell is alive or dead.

A biological material to which the quantification method using the "unimolecular FRET probe" of the present invention is to be applied is not limited to any particular kind. Preferably, the biological material is a material derived from a plant or an animal, more preferably a material derived from an animal such as one selected from fish, amphibians, reptiles, birds, and mammals, particularly preferably a material derived from a mammal. The mammal is not limited to any particular kind and includes: laboratory animals such as mice, rats, rabbits, guinea pigs, and primates except for humans; pet animals such as dogs and cats; farm animals such as cows and horses; and humans.

Alternatively, the biological material may be an individual itself (except for a living human individual). Further alternatively, the biological material may be an organ tissue or a cell taken from an individual of a multicellular organism. As described later, combining with a "clearing reagent for making a biological material transparent" allows making a biological material transparent. Therefore, even if the biological material is a tissue or organ (for example, the whole of or part of the brain) derived from a multicellular animal or an individual itself (for example, an embryo) of a multicellular animal which is not a human, the unimolecular FRET probe allows quantification of autophagy activity.

As described above, the biological material may be either of (i) a material fixed for a microscopic observation and (ii) a non-fixed material. In a case of using a fixed material, the material is preferably immersed in, for example, a 20% (w/v) sucrose-PBS solution, adequately (for example, for 24 hours or more) after being subjected to a fixing process. Furthermore, this material is preferably embedded into an OCT compound and frozen with liquid nitrogen, thawed in PBS, and then fixed again by a 4% (w/v) PFA-PBS solution.

In the method, the sample is irradiated with excitation light having a predetermined wavelength which excites the donor. The wavelength of the excitation light is 400 nm to 440 nm.

The method is intended for the quantification of autophagy activity. Accordingly, it is necessary in the method to determine an intensity of fluorescence emitted from each of the donor and the acceptor. The fluorescence emitted from each of the donor and the acceptor is detected with use of a fluorescence microscope, and a fluorescence intensity of the fluorescence is converted into a numerical value. This intensity is represented as a value obtained by dividing an intensity of a detected fluorescent signal by an intensity of a detected excitation light. Further, a value obtained by dividing a value representing a fluorescence intensity of the donor by a value representing a fluorescence intensity of the acceptor is regarded as a degree of autophagy activity. The degree is obtained with respect to an entire field of view of a fluorescence image.

(Method for Quantifying Mitophagy)

The method for quantifying mitophagy differs from the item "(Method for quantifying autophagy)" in that (i) a unimolecular FRET probe including a mitochondrial localization sequence is used and (ii) mitochondria is the only subject of observation. Accordingly, matters to be described in this item is identical to the descriptions in "(Method for quantifying autophagy)," except that "autophagy" is replaced by "mitophagy" and "(Subject to be analyzed for autophagy)" is replaced by "mitochondrial localization sequence." Therefore, detailed explanation is omitted by citing "(Method for quantifying autophagy)."

[Combination with Method for Clearing Treatment]

A sample including the unimolecular FRET probe may be subjected to a clearing treatment. Subjecting the sample to a clearing treatment allows conducting an observation of a deep part of the sample. Examples of the clearing treatment may include subjecting a sample to a clearing treatment with use of at least one compound selected from the group consisting of urea and a urea derivative, preferably with use of a solution (hereinafter simply referred to as a clearing reagent for making a biological material transparent) containing urea as an active ingredient, as described in, for example, International Publication No. WO2011/111876A1 (U.S. application Ser. No. 13/583,548), International Publication No. WO2012/147965A1 (U.S. application Ser. No. 14/113,639), or International Publication No. WO2012/161143A1 (U.S. application Ser. No. 14/118,150). The clearing reagent for making a biological material transparent is preferably an aqueous solution.

The "clearing reagent for making a biological material transparent" may further include sorbitol as necessary. In a case of using sorbitol, a content of the sorbitol is not particularly limited but preferably in a range of not less than 15 (w/v) % but not more than 50 (w/v) %, more preferably in a range of not less than 18 (w/v) % but not more than 48 (w/v) %. In a case of using sorbitol, the content of Japanese Patent Application Tokugan No. 2015-008928 can also be referred to.

Note that the contents of International Publication No. WO2011/111876A1, International Publication No. WO2012/147965A1, International Publication No. WO2012/161143A1, and Japanese Patent Application Tokugan No. 2015-008928 are incorporated by reference herein in their entireties.

EXAMPLES

Hereinafter, the present invention will be described in more detail with reference to the examples below, although the scope of the present invention is not limited by the descriptions of the Examples.

Example 1: Donor Protein Emitting Fluorescence Under Acidic Condition (Production of Donor Candidate)

As a material for producing a donor candidate, mAG (Karasawa et al., (2003) J Biol Chem. 278, 34167-34171), which is a monomeric mutant of Azami-Green (a fluorescent protein isolated from a meandrinid of the order Scleractinia and emitting green fluorescence) was selected.

In accordance with a previously reported protocol (Sawano, A. et al., (2000) Nucleic Acids Research 28, e78) etc., a polynucleotide encoding a mutated mAG (humanized mAG407, hereinafter simply referred to as "mAG407" (SEQ ID: 4)) was obtained based on mAG. Oligonucleotide-directed mutagenesis was conducted with respect to mAG407 to obtain a polynucleotide encoding a modified mAG further having mutations T58S and V60S and T82A and R184S and K199E and Y210C and Y217A. The modified mAG was named a Humanized Acid Fast Fluorescent Protein (hereinafter simply referred to as AFFP (SEQ ID NO: 1)). These polynucleotides thus obtained were each subcloned into pcDNA3 and HAtag-pcDNA3 so as to be expressed in mammalian cells and compared in terms of fluorescence intensity. The numbers indicating the amino acid positions (58, 60, 82, 142, 173, 182, 184, 199, 210 and 217) are counted from the second position of SEQ ID NOs: 1 and 4.

(Determination of Properties of Donor Candidate)

Whether or not the produced donor candidate possessed properties that are expected of the donor in accordance with the present invention was confirmed in the following manner.

<Fluorescence Intensity>

AFFP and mAG407 were expressed in *Escherichia coli* (18° C.) and a mammalian cell (Mouse embryonic fibroblast (MEF) cell) (37° C.) so as to be compared with each other in terms of fluorescence intensity. Comparison of fluorescence intensity between AFFP and mAG407 which were expressed in *Escherichia coli* was conducted in accordance with a previous report (Katayama, H, et al., (2008) Cell Struct. Funct. 33, 1-12). The concentrations of purified recombinant proteins were adjusted to coincide with each other, and the fluorescence intensity of each fluorescent protein was measured in a buffer at pH 7.0. A test conducted with respect to a protein expressed in *Escherichia coli* in accordance with the aforementioned Katayama, H, et al. will be hereinafter simply referred to as "*Escherichia coli* test."

Comparison of fluorescence intensity in a mammalian cell was conducted in the following manner. A plasmid DNA of each of HA-tag-AFFP/pcDNA3 and HA-tag-mAG407/pcDNA3 was introduced into MEF cells with use of Lipofectamine (Registered Trademark) 2000. One day after the introduction, the cells were collected, a cell lysate was prepared, and fluorescence intensity and protein expression level were measured. The protein expression level was measured by western blotting using an anti-HA antibody (a rat monoclonal antibody, clone 3F10, Roche). The comparison of fluorescence intensity was performed on the basis of correction of actually measured values of fluorescence intensity with use of the protein expression levels. As stated above, a test conducted with respect to proteins expressed in MEF cells will be hereinafter simply referred to as "MEF cell test."

Both in the *Escherichia coli* test and the MEF cell test, AFFP was excited with use of excitation light having an excitation peak wavelength (406 nm) and mAG407 was excited with use of excitation light having an excitation peak wavelength (407 nm), in the measurement of fluorescence intensity. Further, both in the *Escherichia coli* test and the MEF cell test, the intensity of fluorescence emitted from AFFP was set to 1 in numerical representation and plotting of fluorescence intensity.

The results are shown in FIG. 1. An upper stage of FIG. 1 represents results of recombinant proteins purified from *Escherichia coli*, a middle stage of FIG. 1 represents results of fluorescent proteins expressed in MEF cells, and a lower stage of FIG. 1 represents results obtained by comparing numerical representations of the above results. As is clear from FIG. 1, AFFP exhibited fluorescence intensity which was 2.5 times the fluorescence intensity of mAG407 in the *Escherichia coli* test, and exhibited fluorescence intensity which was as high as 14 times the fluorescence intensity of mAG407 in the MEF cell test. It was thus revealed that AFFP was suitable as the donor in accordance with the present invention in terms of high fluorescence intensity.

<Confirmation of Stability of Fluorescence Intensity Against pH Change>

Subsequently, in order to examine the stability of fluorescence intensity of AFFP under an acidic condition, fluorescence intensities exhibited by AFFP in neutral to acidic conditions were measured. As a control for AFFP, a protein was selected as appropriate from green fluorescent proteins (EGFP and Sapphire), a yellow fluorescent protein (Ypet), and red fluorescent proteins (mCherry and Tag-RFP).

With use of EGFP and mCherry as controls, an *Escherichia coli* test was conducted to examine pH dependency of a change in fluorescence intensity of AFFP. In the *Escherichia coli* test, fluorescence intensity of a purified recombinant protein obtained was measured under nine pH conditions ranging from pH 4.0 to 8.0 with an increment of 0.5. The fluorescence intensity of each fluorescent protein under each pH condition was plotted. Note that the plotting was performed in such a manner that a maximum fluorescence intensity of each fluorescent protein was set to 1, and fluorescence intensities of the fluorescent protein under other pH conditions were plotted as relative values with respect to 1.

With use of EGFP, Sapphire, Ypet, mCherry, and Tag-RFP as controls, an *Escherichia coli* test was conducted to examine pH dependency of a change in fluorescence intensity of AFFP. In the *Escherichia coli* test, fluorescence intensities in respective cases of pH 7.0 and pH 4.0 were measured. Then, fluorescence intensities of the fluorescent proteins under the two pH conditions were compared. Note that the fluorescence intensity of each protein at pH 7.0 was set to 1.

In the two measurements above of fluorescence intensity, the excitation wavelength/the fluorescence wavelength of each protein are as follows. AFFP: 410 nm/498 nm, EGFP: 490 nm/507 nm, Ypet: 500 nm/530 nm, Sapphire: 400 nm/510 nm, mCherry: 580 nm/610 nm, TagRFP: 550 nm/584 nm.

Figure 2:
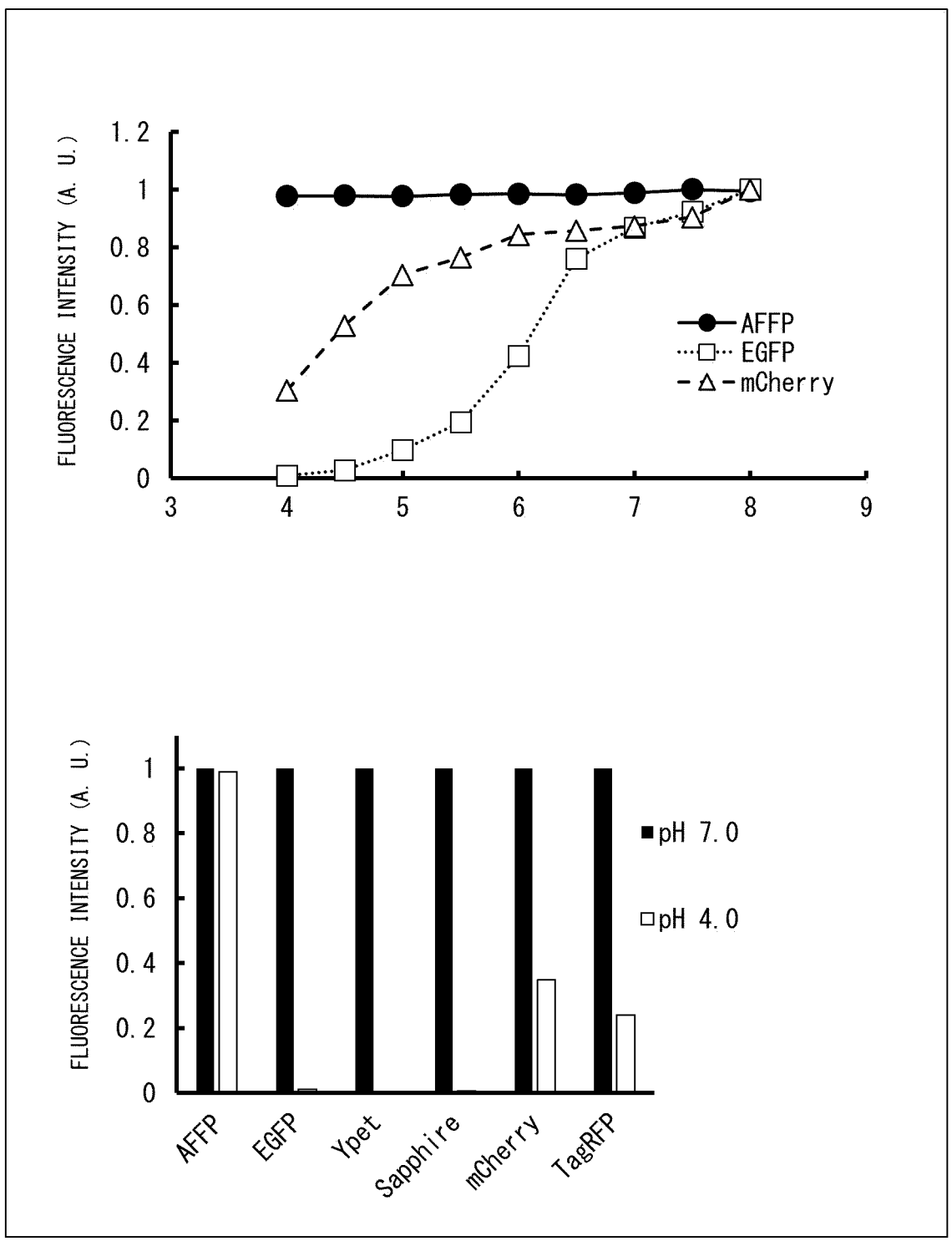
FIG. 2 is a view showing a result from comparison between resistance under an acidic condition of a donor candidate in accordance with the present invention and that of a conventional fluorescent protein.

Results of the two tests above are shown in FIG. 2. In FIG. 2, an upper stage represents results of the *Escherichia coli* test conducted with use of the two controls, and a lower stage represents results of the *Escherichia coli* test conducted with use of the five controls. As is clear from the upper stage of FIG. 2, AFFP has substantially constant fluorescence intensity at pH 4.0 to pH 8.0, unlike EGFP and mCherry. As is clear from the lower stage of FIG. 2, AFFP has fluorescence intensity which is not affected by a change in pH even in further comparison with Ypet, Sapphire, and TagRFP. That is, AFFP was suitable as the donor in accordance with the present invention in terms of having fluorescence intensity independent of a change in pH.

<Confirmation of Resistance to Degradation by Acidic Protease>

An *Escherichia coli* test was conducted which included a treatment of incubating purified recombinant proteins in each of three reaction buffers (pH 7.0/no pepsin, pH 4.0/no pepsin, pH 4.0/0.05% pepsin). The reaction buffers had been prepared as 25 mM HEPES buffer (pH 7.0) or 25 mM acetic acid buffer (pH 4.0) (119 mM NaCl, 2.5 mM KCl, 2 mM $CaCl_2$, 2 mM $MgCl_2$, and 30 mM glucose). A mixture obtained by adding each purified protein to each of the reaction buffers was incubated at 37° C. for 2 hours. The mixture was divided into two, each of which was then subjected to fluorescence intensity measurement and western blotting. The fluorescence intensity measurement was conducted after the pH of the mixture was prepared by diluting the mixture by 200 folds with use of a buffer at pH 7.0. For detection of a protein by means of western blotting, the following antibodies were used. AFFP: a rabbit anti-Azami-Green antibody (MBL, PM052M). EGFP and Ypet: a rabbit anti-GFP antibody (CST, #2555).

Figure 3:
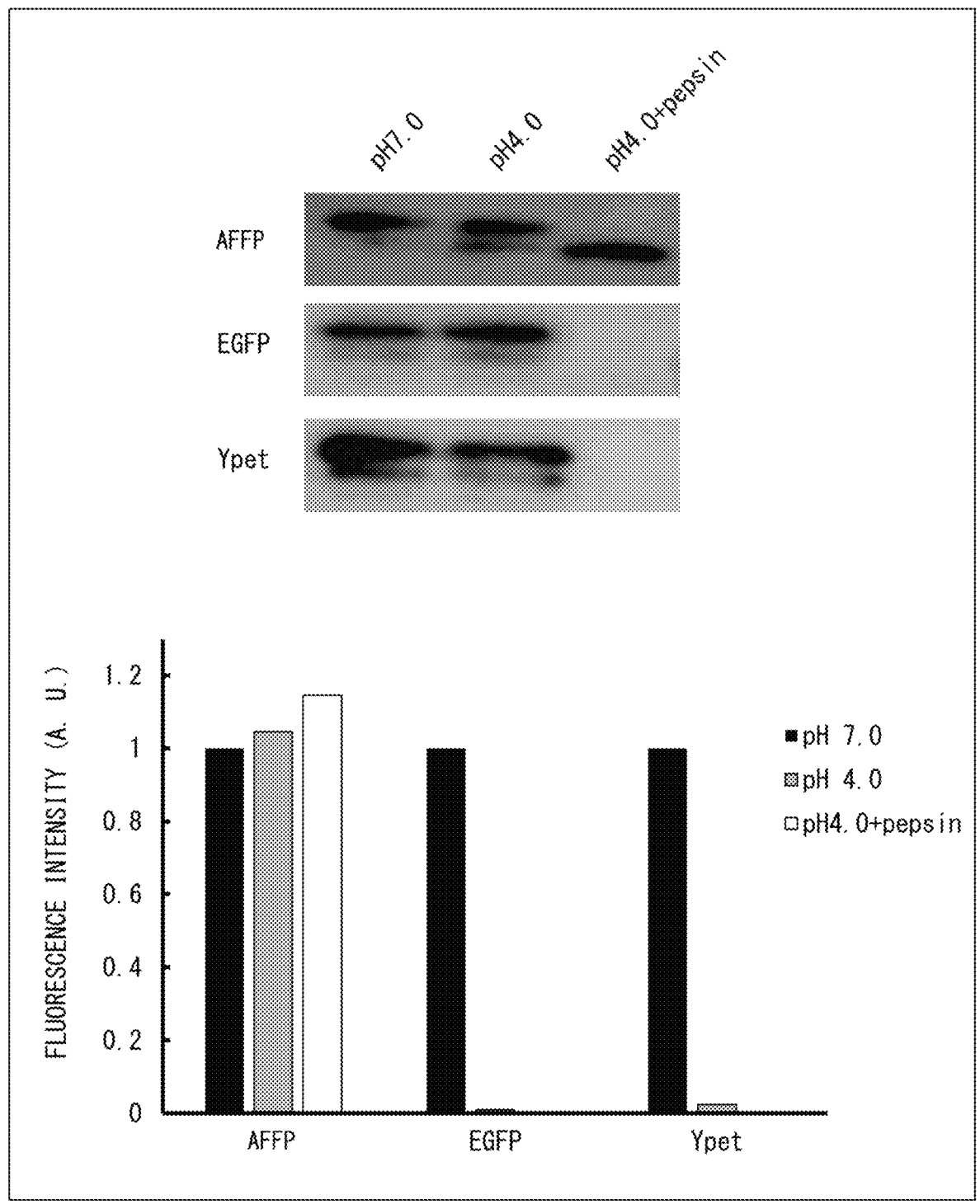
FIG. 3 is a view showing another result from comparison, based on western blotting and fluorescence measurement, between resistance under an acidic condition of the donor candidate in accordance with the present invention and that of a conventional fluorescent protein.

The results are shown in FIG. 3. An upper stage of FIG. 3 represents results obtained by detecting, by western blotting, three proteins exposed under different conditions. A lower stage of FIG. 3 represents results obtained by measuring fluorescence intensities of the three proteins exposed under different conditions. As shown in the upper stage of FIG. 3, conventional fluorescent proteins are degraded by acidic protease, whereas AFFP is not degraded by acidic protease. The lower stage of FIG. 3 shows that this point is evident, and also reconfirms stability of fluorescence intensity in an acidic condition. Thus, it was revealed that AFFP exhibits strong resistance to degradation by acidic protease.

(Evaluation of Resistance of Two Fluorescent Proteins to Degradation Using AFFP-Link-mCherry)

As shown in FIG. 2, between the conventional fluorescent proteins, mCherry had high fluorescence intensity in an acidic condition. In view of this, experiments were conducted in the following manner to evaluate which of AFFP and mCherry would exhibit a higher resistance to degradation by acidic protease.

A fluorescent protein having resistance to an acidic environment and lysosome protease accumulates in a lysosome lumen by autophagy so as to form a structure (called a dot) with high luminance. AFFP and mCherry were compared with each other in terms of this dot-forming ability. In order to compare the dot-forming abilities of AFFP and mCherry under the same condition and in the same cells, mCherry-linker-AFFP was produced. The use of this fusion protein enables evaluation in the same cells and under the same condition without a difference between expression levels of mCherry and AFFP.

First, (i) a BamHI/SacI fragment of mCherry, which fragment contained no stop codon, (ii) a SacI/XhoI fragment of a $(GGGGS)^3$ linker (SEQ ID NO: 5), and (iii) a XhoI/EcoRI fragment of AFFP were ligated to a BamHI/EcoRI fragment of pcDNA3, so that mCherry-linker-AFFP/pcDNA3 was produced. MEF cells were inoculated onto a 35 mm φ glass bottomed dish, and cultured overnight in a DMEM medium containing 5% fetal bovine serum. mCherry-linker-AFFP/pcDNA3 plasmid DNAs were introduced into the MEF cells with use of Lipofectamine (Registered Trademark) 2000 (Gibco, BRL). Twenty-four hours after the introduction, the medium was replaced by HBSS, and culture was conducted at 37° C. for 4 hours to induce autophagy. Then, an image was obtained with use of FV1000 (Olympus). Since the lysosome lumen was acidic (pH 4 to 5), an image after neutralization of the lysosome lumen by a treatment with 50 mM NH4Cl was also taken in order to eliminate an influence on a decrease in fluorescence intensity caused by the acidity. The images obtained were analyzed with use of FV10-ASW (Olympus), and "fluorescence luminance of a dot/fluorescence luminance of a cytoplasm" in each fluorescent protein was compared with each other as an index of dot-forming ability.

Figure 4:
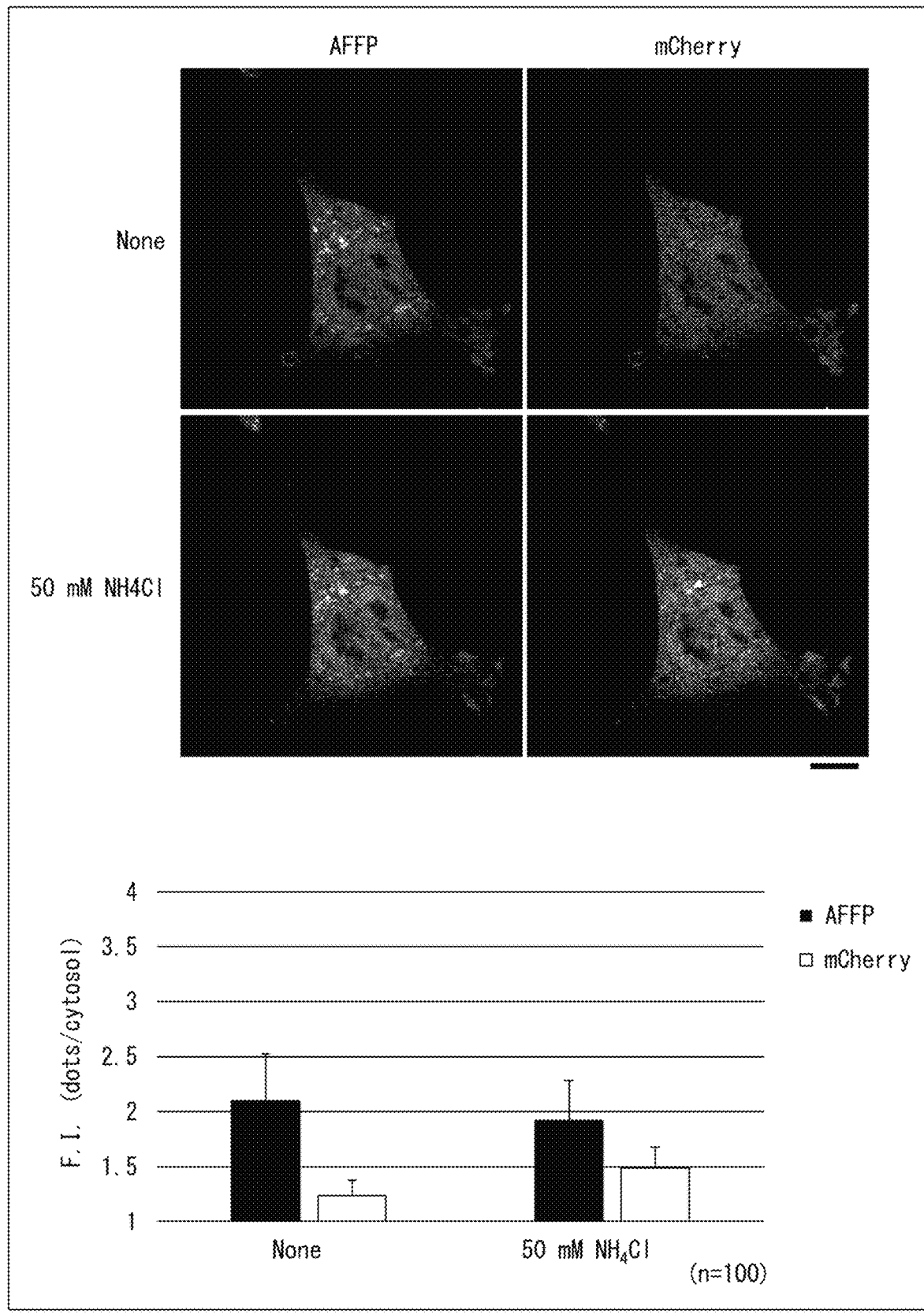
FIG. 4 is a view showing a result obtained by (i) producing a construct in which AFFP is connected with mcherry and (ii) comparing the number of dots of AFFP or mCherry in cells so as to evaluate resistances of AFFP and mCherry against degradation.

Results of the comparison are shown in FIG. 4. An upper stage of FIG. 4 represents four images obtained, and a lower stage of FIG. 4 represents results obtained by numerical representation of dot-forming ability. As shown in FIG. 4, the dot-forming ability of AFFP did not show a significant difference between an acidic condition and a neutral condition. Meanwhile, new dots emerges in mCherry in accordance with neutralization, but the dot-forming ability exhibited by mCherry is lower than that of AFFP. Thus, it was revealed that AFFP has higher resistance to degradation by acidic protease as compared with a conventional fluorescent protein.

As a result of the tests above, it was revealed that AFFP is extremely suitable as the donor in accordance with the present invention in terms of all of (i) high fluorescence intensity, (ii) stable fluorescence intensity independent of pH, and (iii) high resistance to degradation by acidic protease. Accordingly, AFFP was employed as the donor in the unimolecular FRET probe in accordance with the present invention.

Example 2: Unimolecular FRET Probe of Basic Skeleton (Production of Autophagy Probe "Signal Retaining Autophagy Indicator" (SRAI))

Characteristics of AFFP was utilized to design, in the following manner, an SRAI (Signal Retaining Autophagy Indicator) of a FRET probe obtained by combining two fluorescent proteins significantly differing from each other in protease sensitivity under an acidic condition. A schematic arrangement of the SRAI is shown in an upper stage of FIG. 5.

AFFP was combined with YFP of a FRET pair so as to produce a probe which enables more sensitive and quantities detection of autophagy and visualization of the autophagy. Thorough research of the order of arrangement, the types of YFP, and the linker part, it was found that a probe (Ypet-Linker-AFFP (SRAI; SEQ ID NO: 2)) obtained by ligating Ypet, a (GGGGS)$^3$ linker (SEQ ID NO: 5), and AFFP in this order was superior in terms of fluorescence intensity and the like. An *Escherichia coli* expression vector (SRAI/pRSET$_B$) used in the research, had been produced by ligation of a BamHI/SacI fragment of Ypet, a SacI/XhoI fragment of a (GGGGS)$^3$ linker, a XhoI/EcoRI fragment of AFFP, and a BamHI/EcoRI fragment of pRSET$_B$ together.

With use of SRAI/pRSET$_B$, the same procedure as the fluorescence intensity measurement in the item <Confirmation of resistance to degradation by acidic protease> was carried out. Fluorescence intensity measurement was conducted by irradiating the AFFP part in SRAI with excitation light of 410 nm and irradiating the Ypet part in SRAI with excitation light of 500 nm.

Figure 5:
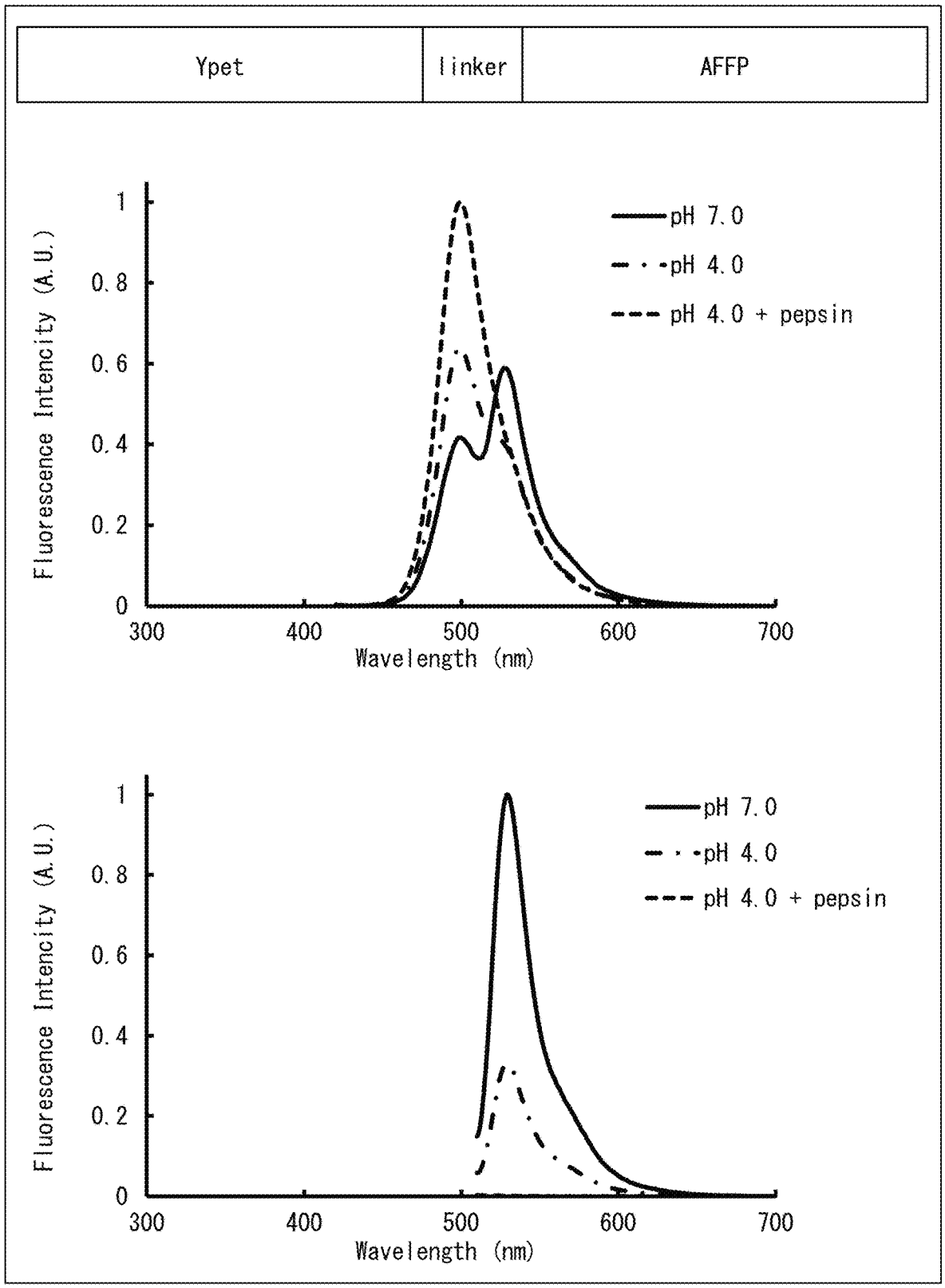
FIG. 5 is a view whose upper stage schematically illustrates an arrangement of an autophagy probe SRAI and whose middle and lower stages show a result obtained by (i) subjecting SRAI to a treatment conducted prior to fluorescence measurement in FIG. 2 and (ii) then measuring fluorescence intensity of SRAI.

The results are shown in FIG. 5. A middle stage of FIG. 5 shows results obtained by exciting AFFP under three conditions, and a lower stage of FIG. 5 shows results obtained by exciting Ypet under three conditions. As shown in the middle stage of FIG. 5, in a case of irradiation with excitation light of 410 nm, SRAI in a neutral condition showed two peaks that were based on fluorescence from both AFFP and Ypet which was provided with energy from AFFP. SRAI exhibited a reduction in peak of fluorescence from Ypet in an acidic condition. In an acidic condition with pepsin added, SRAI showed only a single peak that was based on fluorescence from AFFP.

Meanwhile, as shown in the lower stage of FIG. 5, in a case of irradiation with excitation light of 500 nm, SRAI exhibited a single intense peak in a neutral condition, and a single weak peak in an acidic condition. Further, SRAI emitted no fluorescence in an acidic condition with pepsin added. This is because Ypet had been degraded, as shown in FIG. 3.

Thus, it was revealed that SRAI is an extremely excellent probe for quantifying autophagy activity. Since it was confirmed that SRAI was an excellent probe, a polynucleotide (SEQ ID NO: 3) encoding SRAI was subcloned into a vector (pcDNA3) for expression in mammalian cells, thereby obtaining SRAI/pcDNA3.

(Detection of Autophagy in Mammalian Cells Using S)

SRAI/pcDNA3 was introduced into MEF cells so as to express SRAI therein, and whether or not SRAI was suitable for observation of autophagy was evaluated. As a control, mCherry-EGFP was used. In order for mCherry-EGFP to be equivalent to an amino acid sequence presented in a previous report (Elsa-Noah N'Diaye, et al., (2009) EMBO reports 10, 173-179), (i) a BamHI/HindIII fragment of mCherry, which fragment contained no stop codon, (ii) a HindIII/EcoRI fragment of EGFP, in which fragment cDNA encoding a linker (SGLRSAGPGTSLYKKAGFPVAT) (SEQ ID NO: 6) at N-terminus was added, and (iii) a BamHI/EcoRI fragment of pcDNA3 were ligated with each other, thereby producing mCherry-EGFP/pcDNA3. With use of Lipofectamine (Registered Trademark) 2000, SRAI/pcDNA3 or mCherry-EGFP/pcDNA3 was introduced into MEF cells. One day after, the medium was changed from a DMEM medium (nutrient medium) containing 5% fetal bovine serum to HBSS, and culture was conducted at 37° C. for 2 hours to induce autophagy. A control group was cultured in the nutrient medium without change.

In imaging, Cool SNAP HQ2 (Photometrics) was used as a camera, UplanF1 40× oil N.A.1.30 (Olympus) was used as an objective lens, and U-MCFPH Q (for AFFP), U-MYFPH Q (for Ypet), U-MRFPH Q (for mCherry), and U-MGFPH Q (for EGFP) were used as filter cubes (each cube is manufactured by Olympus). Images were obtained and analyzed with use of MetaMorph (Universal Imaging Corporation). Ratio images of SRAI and ratio images of mCherry-EGFP were generated on the basis of AFFP/Ypet and mCherry/EGFP, respectively, in IMD display in a range of 0 to 1.

Figure 6:
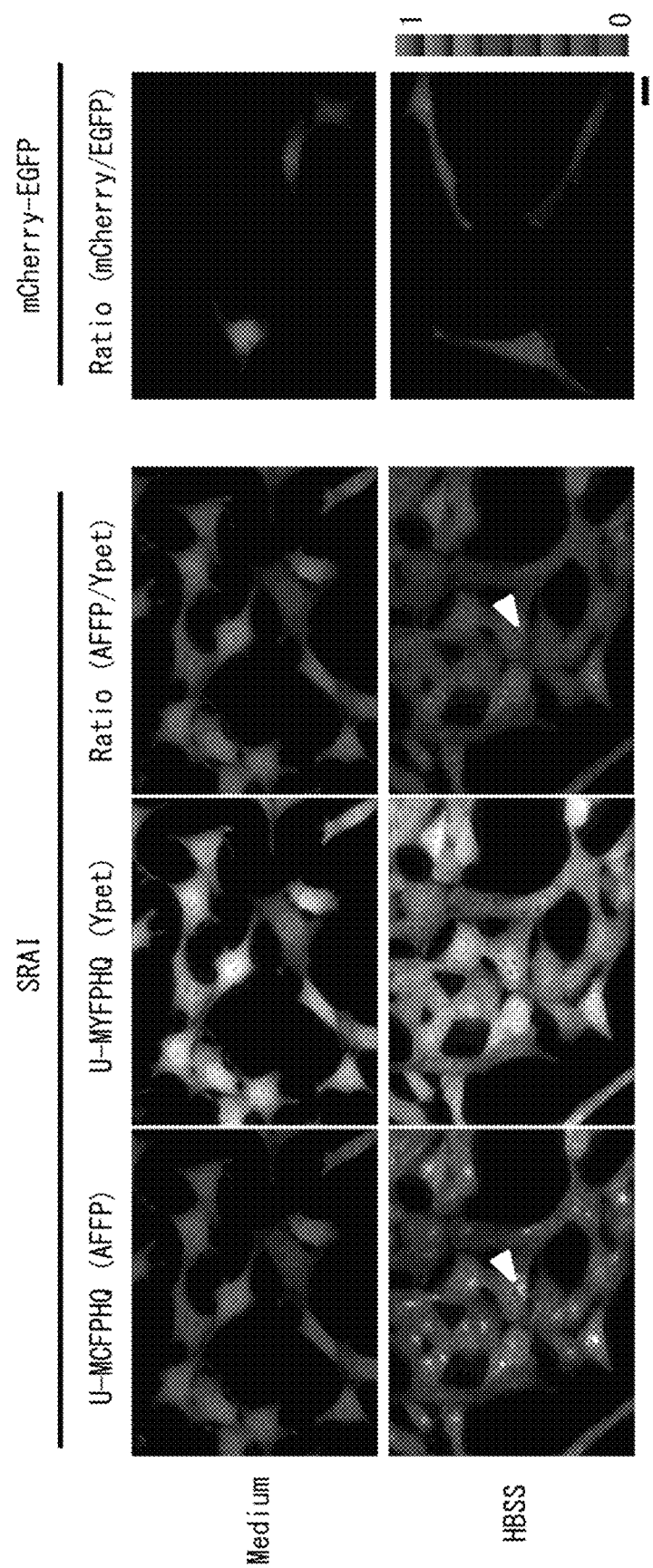
FIG. 6 is a view showing a result obtained by quantifying autophagy activity in a cultured cell with use of the probe shown in FIG. 5.

The results are shown in FIG. 6. FIG. 6 shows results obtained by quantifying autophagy activity in cultured cells with use of SRAI and mCherry-EGFP. The scale bar for FIG. 6 is 20 μm. As shown in FIG. 6, as a result of (i) transfer into lysosomes caused by autophagy and (ii) degradation of Ypet, a bright point (dot) and a red point in a ratio image were observed. The bright point and the red point were based on fluorescence from AFFP. Meanwhile, hardly any bright point and red point were observed in cells in which mCherry-EGFP was expressed. Thus, it was revealed that SRAI allows autophagy activity to be quantified well.

(Detection of Autophagy in Fixed Mammalian Cells)

Subsequently, examination was conducted to examine whether or not SRAI would detection of autophagy also in fixed cells. The same operations as those of the autophagy detection above were conducted, except that (i) only SRAI was observed and (ii) after observation of living cells, the cells were fixed and observed again in the same field of view. The living cells were fixed for 15 minutes at room temperature in PBS containing 4% PFA, and cells thus fixed were subjected to washing with use of HBSS (5 minutes×3 times) and then subjected to observation for the second time.

Figure 7:
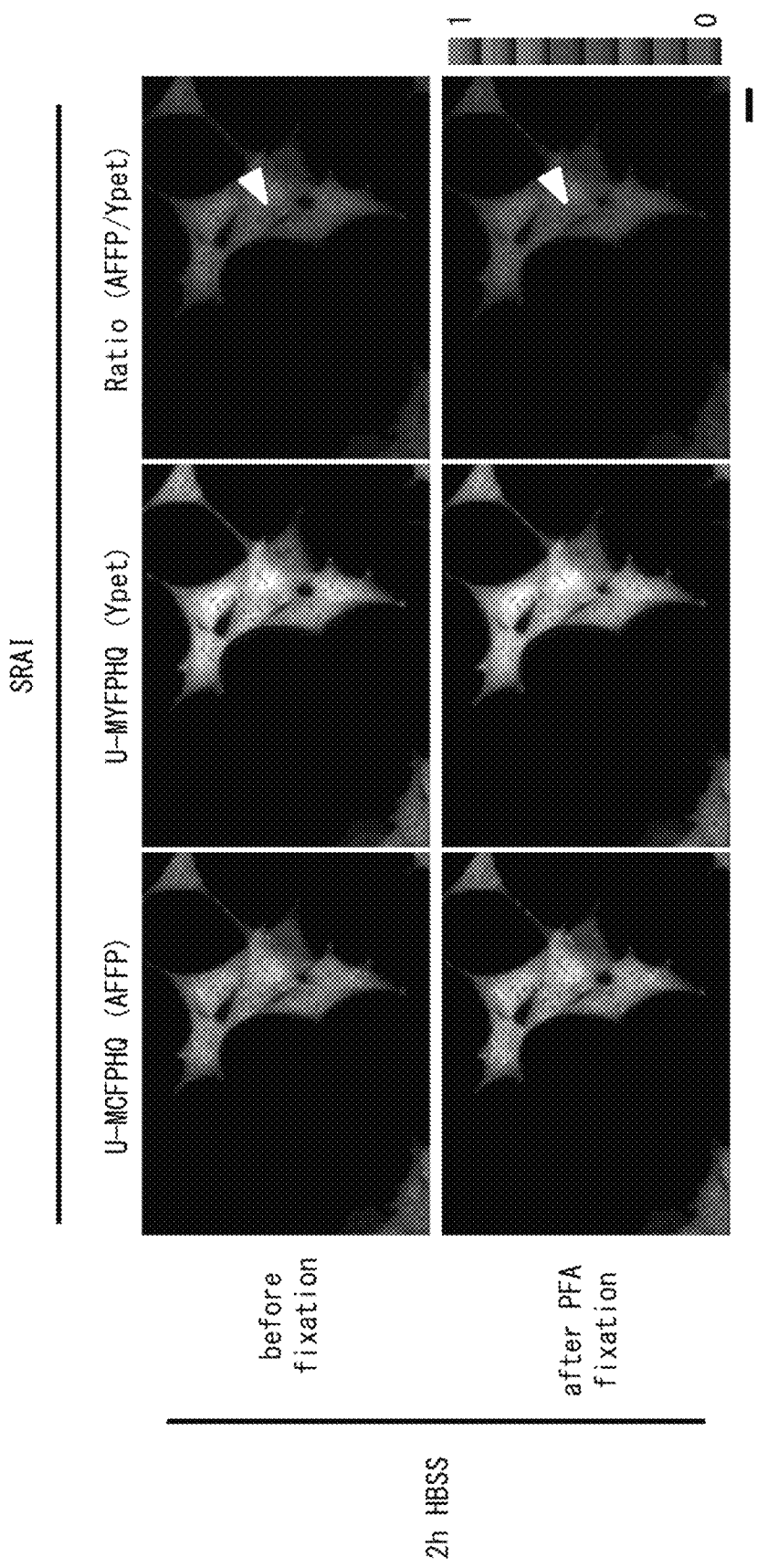
FIG. 7 is a view showing a result obtained by quantifying, with use of the probe shown in FIG. 5, autophagy activity in a cultured cell after the cell was fixed.

FIG. 7 shows results obtained by quantifying autophagy activity in cultured cells with use of SRAI after the cells had been fixed. The scale bar for FIG. 7 is 20 μm. As shown in FIG. 7, little change was observed between images taken before and after the fixation. Thus, it was shown that the use of SRAI allowed detection of a signal of autophagy even after cells had been fixed, similarly as in the case of living cells.

(Detection of Autophagy in an Animal Individual with Use of SRAI)

Then, examination was conducted to examine whether or not SRAI would enable detection of autophagy in an animal individual. A solution obtained by mixing 1 mg/ml SRAI/pcDNA3 and TransIT (Registered Trademark)-QR Hydrodynamic Delivery Solution (Mirus Bio LLC) at a ratio of 1:209 was administered to each of 7-week-old male C57BL6J mice by tail vein injection in an amount of 1/10±0.1 mL of the number of grams of the weight of the mouse. Twenty-four hours after the injection, each mouse was kept for 24 hours under a condition with food (control) or a condition with only water (starvation). Then, the mouse was anesthetized with Somnopentyl in an amount of 1/100 ml of the number of grams of the weight of the mouse, and then was subjected to perfusion fixation with use of PBS containing 4% PFA. A thin slice was prepared from the liver of the mouse, and was subjected to imaging. The imaging was conducted in a similar manner to the imaging of cells, except that UplanApo 20× N.A.0.70 was used as an objective lens. Images were obtained and analyzed in a similar manner to the case of cells. Ratio images were generated in IMD display in a range of 0 to 0.4.

Figure 8:
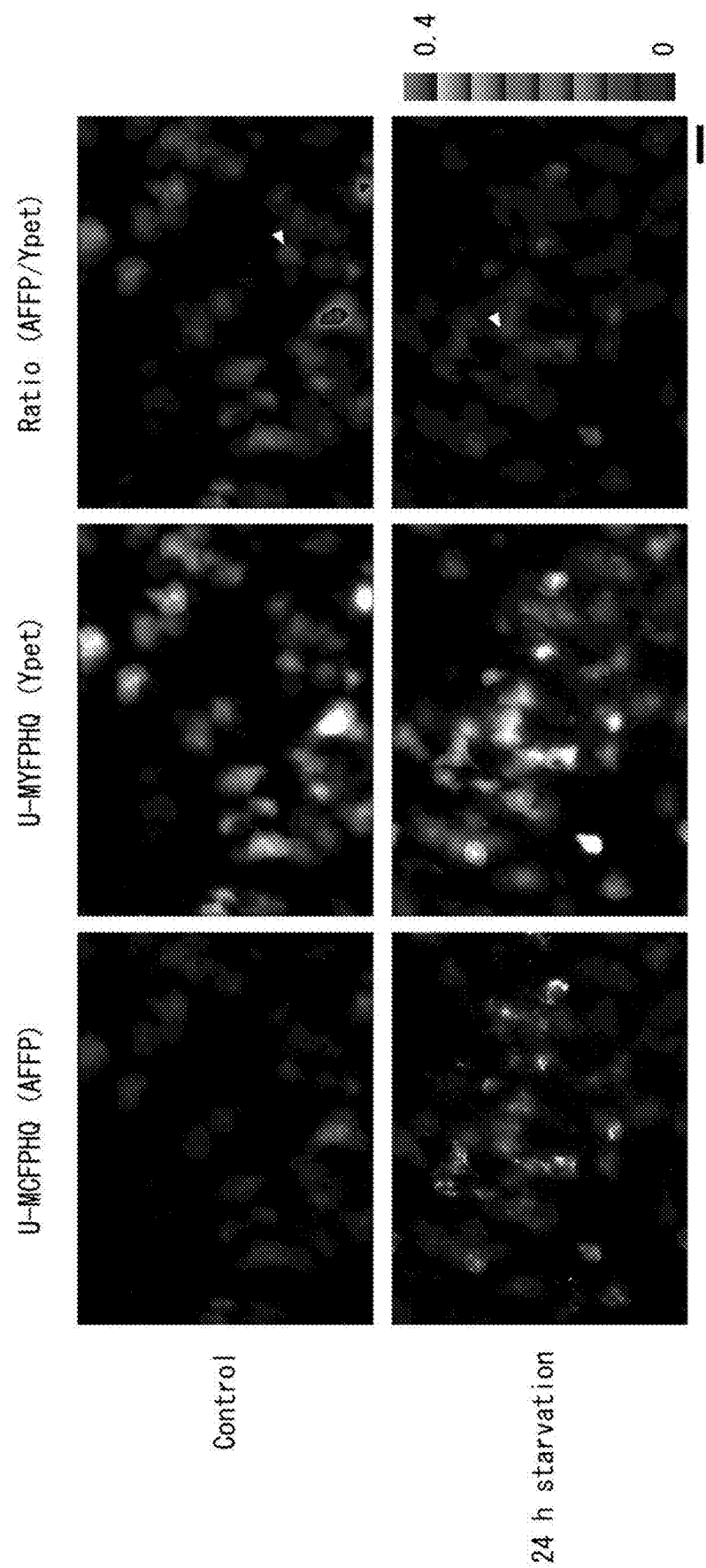
FIG. 8 is a view showing a result obtained by quantifying, with use of the probe shown in FIG. 5, autophagy activity in the liver of a mouse that has undergone 24 hours of starvation.

FIG. 8 shows results obtained by quantifying, with use of SRAI, autophagy activity in the liver of a mouse that had undergone 24 hours of starvation. The scale bar for FIG. 8 is 50 µm. As shown in FIG. 8, a bright point (dot) and a red point in a ratio image, based on fluorescence from AFFP, significantly increased in the control as compared with the starvation. Thus, it was revealed that the use of SRAI allowed detecting a signal of autophagy in an animal individual.

Example 3: Unimolecular FRET Probe for Detection of Mitophagy (Production of Mitochondrial Localization Type SRAI Construct for Detection of Mitophagy)

Next, in order to detect mitophagy (autophagy of mitochondria), a construct expressing a probe with an improved mitochondria-localization property was designed. As the form of the probe, one which is obtained by adding a mitochondrial localization signal sequence to SRAI was assumed.

In order to employ an experimental system similar to that of Katayama, H, et al., (2011) Chem. & Biol. 18, 1042-1052, the following materials were prepared: a polynucleotide encoding a probe in which a sequence (2xCoxVIII signal seq) having two repeating human coxVIII signal peptide sequences (MSVLTPLLLRGLTGSARRLPVPRAK-IHSLPPEG) (SEQ ID NO: 7) is provided on the N-terminus side of SRAI; a vector (pMCSTRE3) for induced expression in mammalian cells; and an expression inducer doxycycline (sigma). Note that in the experimental system above, a construct is introduced into cells, an expression of a protein is induced by an expression inducer, and then the expression inducer is eliminated from the medium, thereby ensuring localization.

A KpnI/BamHI fragment of 2xCoxVIII signal seq, a BamHI/NheI fragment of SRAI, and a KpnI/NheI fragment of pMCSTRE3G were ligated with each other, thereby obtaining a mitochondrial localization type SRAI construct (mt-SRAI/pMCSTRE3G). In place of the fragment of SRAI, a BamHI/NheI fragment of mKeima was used to produce mt-mKeima/pMCSTRE3G, which was used as a control for comparison in terms of localization. Plasmid DNAs of the following combination (1) or (2), were introduced into MEF cells with use of Lipofectamine (Registered Trademark) 2000.
(1) mt-SRAI/pMCSTRE3G and a Tet-On regulatory vector (pEF1α-Tet3G (Takara)), each in an amount of 5 µg
(2) mt-mKeima/pMCSTRE3G and a Tet-On regulatory vector, each in an amount of 5 µg.
Six hours after the introduction, the medium was replaced by a nutrient medium containing 1 µg/mL doxycycline. Twenty-four hours later, induction of expression was stopped, and the medium was replaced by a nutrient medium containing no doxycycline, so that localization of a probe remaining in the cytoplasm was encouraged. Then, imaging was conducted 18 hours later. However, mt-SRAI exhibited a mitochondria localization efficiency (not shown) lower than that of mt-mKeima. This was assumed to have been caused by a great molecular weight of mt-SRAI. Since a probe remaining in the cytoplasm would prevent accurate detection of mitophagy, experiments were conducted to determine such an arrangement of a construct that would enable expression of a probe exhibiting better localization.

A ubiquitin-proteasome system recognizes a degron sequence and carries out specific proteolysis in the cytoplasm. In an attempt to achieve better mitochondria localization, a degron sequence was added to mt-SRAI, thereby causing degradation of a fraction remaining in the cytoplasm. In a mitochondria matrix, no ubiquitin-proteasome exists. Accordingly, a probe which has successfully been localized can avoid being degraded. The use of a degron sequence therefore does not cause any negative effect such as a decrease in fluorescence intensity. In order to consider a possible degron sequence having an adequate degradation-inducing ability, a construct which expresses mt-SRAI and to which the following sequence had been added was produced: a CL1 sequence (ACKNWFSSLSHFVIHL) (SEQ ID NO: 8), an amino acid sequence (PEST sequence: PRSRPMWQLMKQIQSHGFPPEVEEQDDGTLPMS-CAQESGMDRHPAACASARINV) (SEQ ID NO: 9) of the 421-th position to the C-terminus of mouse ornithine decarboxylase, and a combination thereof. Schematic arrangements of probes expressed by the constructs explained above are shown in FIG. 9.

The constructs in FIG. 9 expressing probes each including a degron sequence were produced in the following manner. A KpnI/NheI fragment of mt-SRAI, which fragment included no stop codon, a KpnI/BamHI fragment of pMCSTRE3G, and a XbaI/BamHI fragment of CL1 were ligated with each other, so that mt-SRAI-CL1/pMCSTRE3G was produced. To produce mt-SRAI-PEST/pMCSTRE3G, mt-SRAI-CL1CL1/pMCSTRE3G, or mt-SRAI-CL1PEST/pMCSTRE3G, a XbaI/BamHI fragment of PEST, a XbaI/BamHI fragment of CL1CL1, or a XbaI/BamHI fragment of CL1PEST was used in place of the XbaI/BamHI fragment of CL1.

A plasmid DNA of any one of the constructs above and pEF1α-Tet3G were introduced, each in an amount of 0.5 µg, into MEF cells with use of Lipofectamine (Registered Trademark) 2000. Six hours after the introduction, the medium was replaced by a nutrient medium containing 1 µg/mL doxycycline, and then 24 hours later, the cells were subjected to imaging. For more precise evaluation of localization efficiency, induction of expression was not stopped. The imaging was conducted under the same conditions as those for the detection of autophagy in mammalian cells. Images were obtained and analyzed with use of MetaMorph, and "intranuclear fluorescence intensity (A fluorescence intensity which is equivalent to that of the cytoplasm and with which no fluorescence of mitochondria is mixed due to the absence of mitochondria)/fluorescence intensity of the mitochondria part" was evaluated as an index of localization efficiency.

Figure 10:
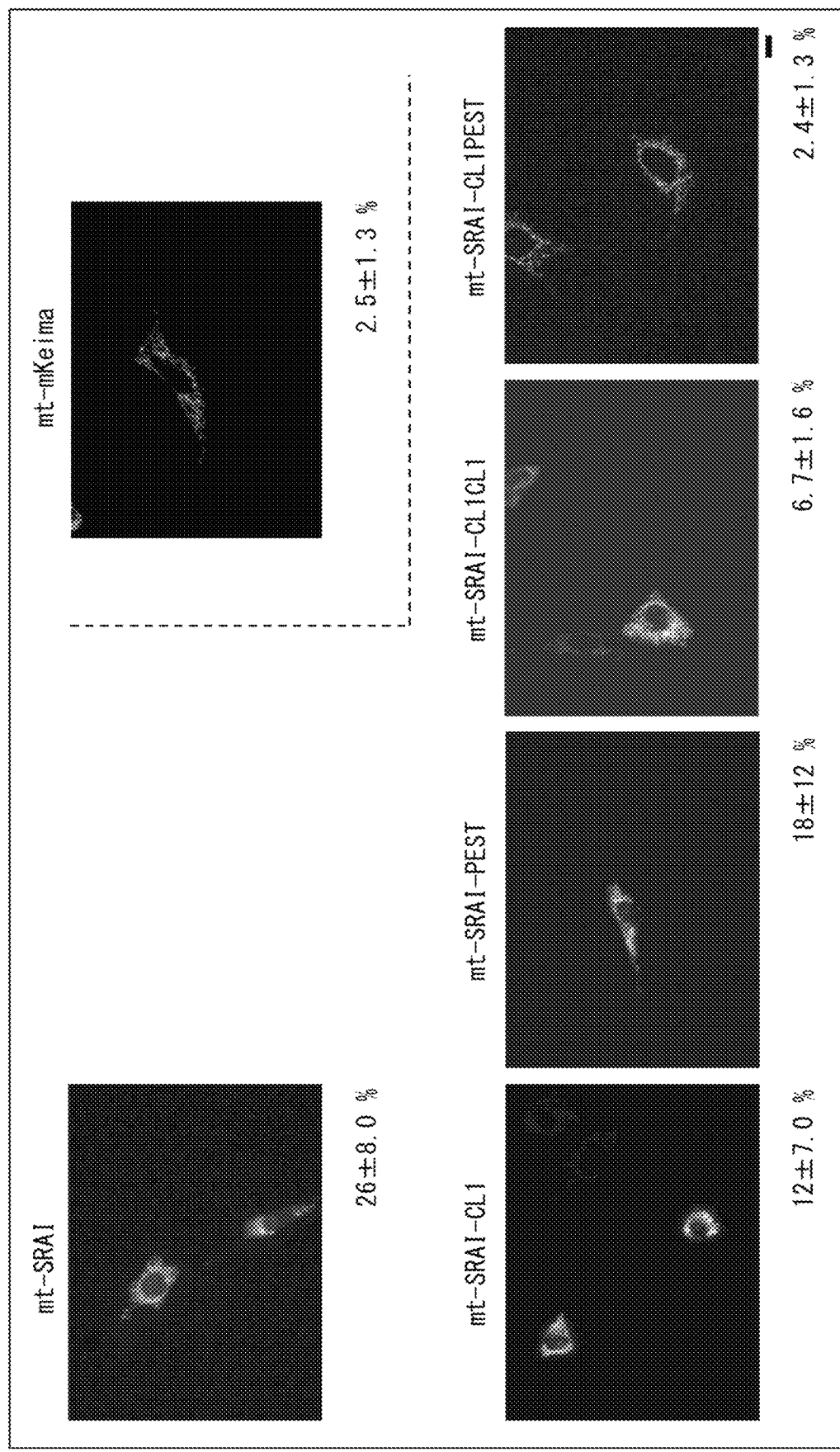
FIG. 10 is a view showing a result obtained by confirming localization to mitochondria with use of probes shown in FIG. 9.

The results are shown in FIG. 10. FIG. 10 shows results obtained by confirming localization of the probes of FIG. 9 to mitochondria. The scale bar for FIG. 10 is 20 µm. The numerical value shown under each panel of FIG. 10 indicates "intranuclear fluorescence intensity/fluorescence intensity of the mitochondria part," wherein the smaller the value, the higher the efficiency of localization to mitochondria. As is clear from FIG. 10, mt-SRAI-CL1PEST exhibited the highest efficiency of localization to mitochondria. As such, mt-SRAI-CL1PEST was used in subsequent tests. The localization efficiency of mt-SRAI-CL1PEST improved to a level equivalent to that of mt-mKeima, as compared with a level before addition of the degron sequence. Hereinafter, mt-SRAI-CL1PEST will be simply referred to as mt-SRAI'.

(Detection of Mitophagy in Mammalian Cells Using Mt-SRAI')

A construct that expresses mt-SRAI' was introduced into MEF cells, in an attempt to visualize and detect mitophagy. mt-SRAI/pMCSTRE3G, pEF1α-Tet3G, and mCherry-Parkin/pcDNA3 which is a factor necessary for mitophagy, were introduced, each in an amount of 0.5 μg, into MEF cells with use of Lipofectamine (Registered Trademark) 2000. Six hours after the introduction, the medium was replaced by a nutrient medium containing 1 μg/ml doxycycline. Twenty-four hours later, induction of expression was stopped, and the nutrient medium was replaced by a nutrient medium containing no doxycycline, so that localization and degradation of a probe remaining in the cytoplasm was encouraged. Eighteen hours later, mitophagy was induced with use of 30 μM carbonyl cyanide m-chlorophenylhydrazone (CCCP), and then 18 hours later, the cells were subjected to imaging. Further, in order to show that signals would not be lost by neutralization of an acidic environment in the cells, 50 mM NH4Cl was added and then images were obtained again. In performing the imaging and obtaining and analyzing the images, the same conditions as those for the detection of autophagy in fixed mammalian cells were applied. Ratio images were generated in IMD display in a range of 0 to 0.4.

Figure 11:
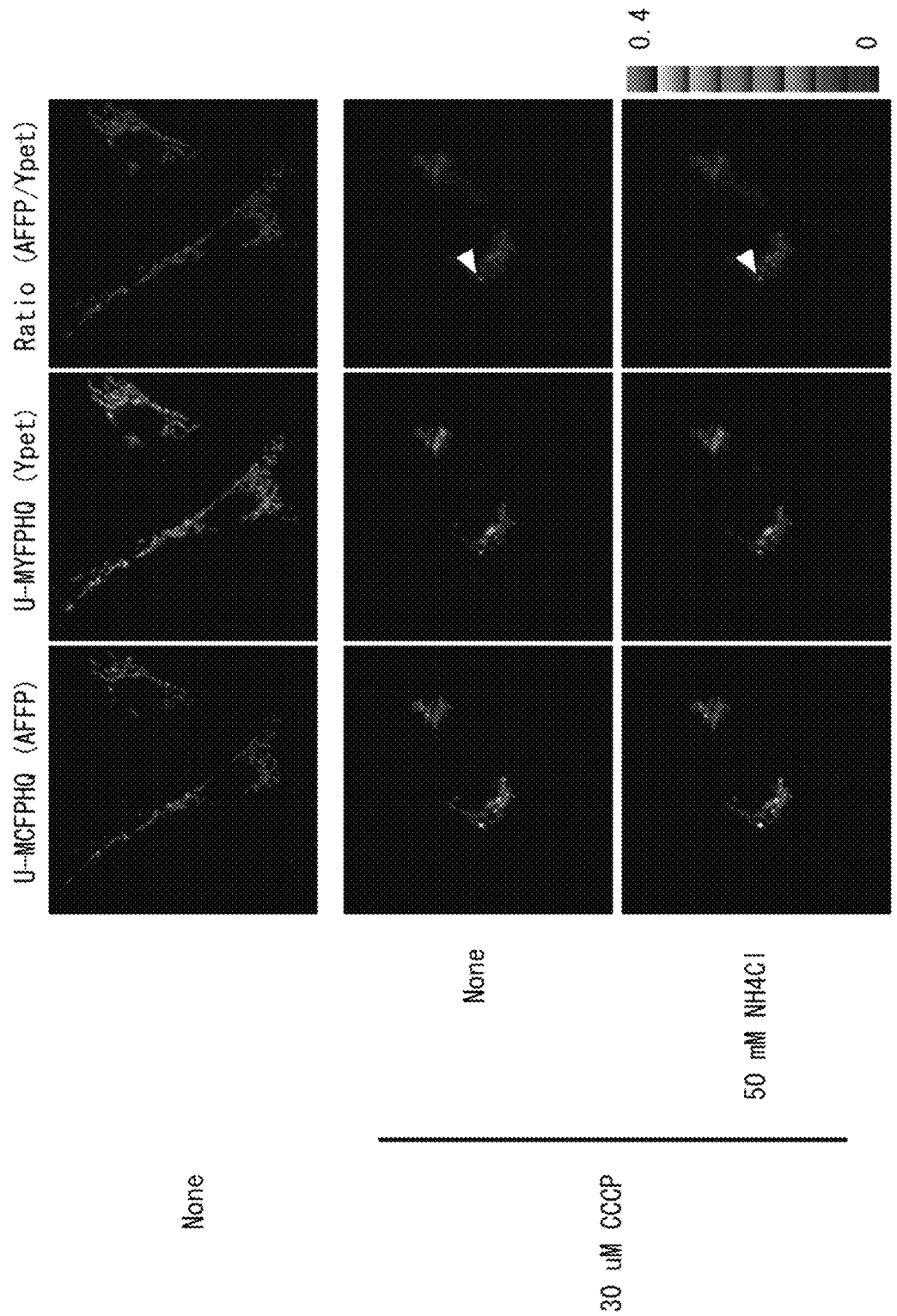
FIG. 11 is a view showing a result obtained by detecting mitophagy with use of a probe shown in FIG. 9.

The results are shown in FIG. 11. FIG. 11 shows results obtained by detecting mitophagy with use of the probes shown in FIG. 9. The scale bar for FIG. 11 is 20 μm. As shown in FIG. 11, as a result of mitophagy induction by CCCP, a significant increase of red points was observed in the ratio images, as compared to before addition of CCCP. Further, even after neutralization of lysosome lumen by NH₄Cl, the signals were not lost. Thus, it was revealed that with use of the unimolecular FRET probe of the present invention, activations of various types of autophagy can be quantified by adding an appropriate sequence to SRAI.

Comparative Example: Evaluation of Resistance of Rosella to Acidic Condition and Acidic Protease, and Detection of Autophagy in Mammalian Cells Experiments were conducted to determine whether or not a probe (Rosella) reported by Rosado et al. was suitable for measuring autophagy as compared with SRAI. A construct of Rosella was expressed in *Escherichia coli*, and a recombinant fluorescent protein was purified. The recombinant fluorescent protein was incubated for 2 hours at 37° C. in a reaction buffer at pH 7.0, a reaction buffer at pH 4.0 (with 0.05% pepsin), and a reaction buffer at pH 4.0 (without 0.05% pepsin) in accordance with a previous report (Katayama, H, et al. (2008) Cell Struct. Funct. 33, 1-12), and was subjected to fluorescence measurement. Before the fluorescence measurement, pHs of these samples were adjusted to coincide with each other by diluting each sample with a buffer (pH 7.0) by 200 folds. The reaction buffers had each been prepared as 25 mM HEPES buffer (pH 7.0) or 25 mM acetic acid buffer (pH 4.0) (119 mM NaCl, 2.5 mM KCl, 2 mM CaCl₂, 2 mM MgCl₂, and 30 mM Glucose). As a result of *Escherichia coli* test, both DsRed.T3 and SEP, which were components of Rosella, undergone a decrease in fluorescence intensity due to an acidic condition (pH 4.0) and a treatment under with acidic protease (see the graph of FIG. 12).

Further, Rosella was introduced into MEF cells in an attempt to visualize and detect autophagy. Rosella/pcDNA3 was introduced into MEF cells with use of Lipofectamine (Registered Trademark) 2000. One day after, the medium was changed from a DMEM medium (nutrient medium) containing 5% fetal bovine serum to HBSS, and culture was conducted at 37° C. for 2 hours, thereby inducing autophagy. The group of controls were cultured in the nutrient medium without a change of medium. For imaging, Cool SNAP HQ2 (Photometrics) was used as a camera, UplanF1 40× oil N.A.1.30 (Olympus) was used as an objective lens, and U-MRFPH Q (DsRed.T3) and U-MGFPH Q (SEP) were used as filter cubes (all of the cubes are manufactured by Olympus). Images were obtained and analyzed with use of MetaMorph (Universal Imaging Corporation), and ratio images were produced as DsRed.T3/SE P in IMD display in a range of 0 to 1 (the scale bar for FIG. 12 is 20 μm).

Figure 12:
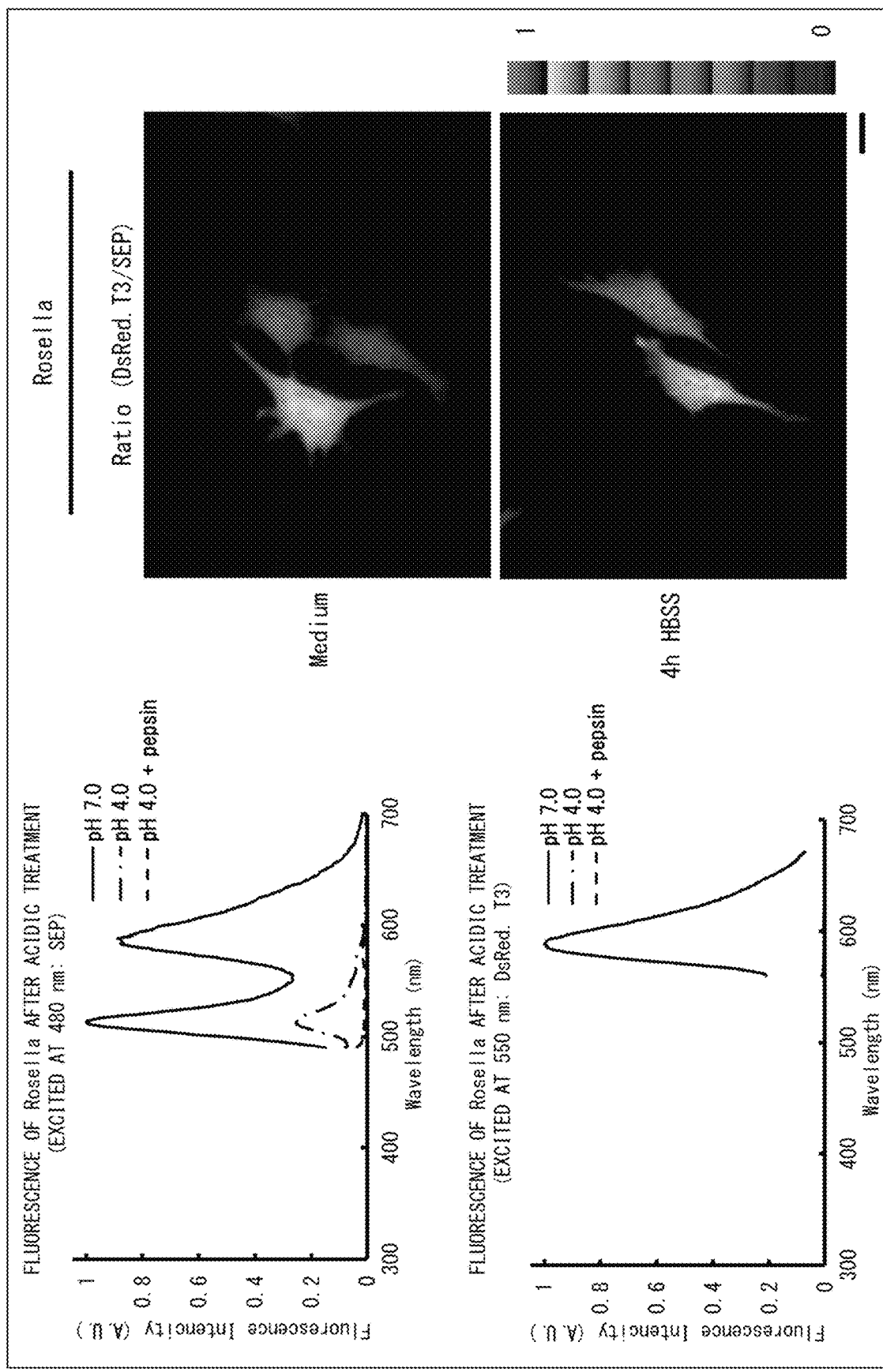
FIG. 12 is a view showing evaluation of a property of a probe (Rosella) reported by Rosado et al.

As shown by the images in FIG. 12, a structure with a high ratio resulting from autophagy, which structure was observed in SRAI, was hardly observed in Rosella.

The present invention is not limited to the above-described embodiments and examples but allows various modifications within the scope of the claims. In other words, any embodiment derived from a combination of two or more technical means appropriately modified within the scope of the claims will also be included in the technical scope of the present invention.

INDUSTRIAL APPLICABILITY

The present invention is applicable to the fields of research, cell engineering, and medical care, for example, for the search for various vital phenomena, the in vitro development of useful cells, the treatment of diseases associated with autophagy, and the like.

The invention claimed is:

1. A unimolecular FRET probe, comprising:
   an acceptor consisting of a fluorescent protein to be enzymatically degraded inside a lysosome or a vacuole; and
   a donor consisting of an amino acid sequence having a sequence identity of 95% or more with respect to SEQ ID NO: 1,
   wherein the following amino acid residues and amino acid positions counted from second position of SEQ ID NO: 1 are in the amino acid sequence of the donor: S58, S60, A82, S184, E199, C210, and A217.

2. The unimolecular FRET probe as set forth in claim 1, wherein the fluorescent protein is a yellow fluorescent protein derived from *Aequorea victoria*.

3. The unimolecular FRET probe as set forth in claim 1, wherein the fluorescent protein is selected from the group consisting of YFP, EYFP, Ypet, Topaz, Citrine, mCitrine, mEYFP, Venus, mVenus, and TagYFP.

4. The unimolecular FRET probe as set forth in claim 1, further comprising a mitochondrial localization sequence.

5. A method for quantifying an activity of autophagy, comprising detecting a fluorescent signal from a cell containing a unimolecular FRET probe recited in claim 1.

6. The method as set forth in claim 5, wherein the cell has been fixed.

* * * * *